(12) United States Patent
Hatakeyama et al.

(10) Patent No.: US 12,419,561 B2
(45) Date of Patent: Sep. 23, 2025

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Osamu Watanabe, Joetsu (JP); Joe Ikeda, Joetsu (JP); Shiori Nonaka, Joetsu (JP); Koji Hasegawa, Joetsu (JP); Motoaki Iwabuchi, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 950 days.

(21) Appl. No.: 17/516,022

(22) Filed: Nov. 1, 2021

(65) Prior Publication Data
US 2022/0133201 A1    May 5, 2022

(30) Foreign Application Priority Data
Nov. 5, 2020 (JP) ................................ 2020-185025

(51) Int. Cl.
*A61B 5/265* (2021.01)
*A61B 5/024* (2006.01)
(Continued)

(52) U.S. Cl.
CPC .......... *A61B 5/265* (2021.01); *A61B 5/02438* (2013.01); *A61B 5/268* (2021.01);
(Continued)

(58) Field of Classification Search
None
See application file for complete search history.

(56) References Cited

U.S. PATENT DOCUMENTS 11,160,480 B2 *  11/2021  Hatakeyama ........... C08L 83/04
2015/0275060 A1  10/2015  Kuroda et al.
(Continued)

FOREIGN PATENT DOCUMENTS

CN   111493863 A   8/2020
CN   111789585 A   10/2020
(Continued)

OTHER PUBLICATIONS

Mazurek et al, How to tailor flexible silicone elastomers with mechanical integrity: a tutorial review, Chem. Soc. Rev., 2019, 48, 1448-1464 (Year: 2019).*

(Continued)

*Primary Examiner* — Randy P Gulakowski
*Assistant Examiner* — Audra J Destefano
(74) *Attorney, Agent, or Firm* — Oliff PLC

(57) ABSTRACT

A bio-electrode composition contains (A) an ionic polymer material, (B) an addition reaction-curable silicone having at least a hydrosilyl group, (C) a platinum-group catalyst, and a solvent. The bio-electrode composition has a water content of 0.2 mass % or less. The solvent includes one or more of an ether solvent, an ester solvent, and a ketone solvent each of which does not contain a hydroxy group, a carboxyl group, a nitrogen atom, or a thiol group. Thus, present invention provides: a bio-electrode composition capable of forming a living body contact layer for a bio-electrode which is excellent in electric conductivity and biocompatibility, light-weight, and manufacturable at low cost, and which does not leave residue on skin after attachment to and peeling from the skin; a bio-electrode including a living body contact layer formed of the bio-electrode composition; and a method for manufacturing the bio-electrode.

22 Claims, 2 Drawing Sheets

(51) Int. Cl.
  *A61B 5/268*  (2021.01)
  *A61B 5/28*   (2021.01)
  *C08F 212/14* (2006.01)

(52) U.S. Cl.
  CPC .......... *A61B 5/28* (2021.01); *A61B 2562/125* (2013.01); *C08F 212/30* (2020.02)

(56) References Cited

U.S. PATENT DOCUMENTS

| | | |
|---|---|---|
| 2016/0155530 A1 | 6/2016 | Someya et al. |
| 2018/0072930 A1 | 3/2018 | Hatakeyama et al. |
| 2018/0085019 A1 | 3/2018 | Hatakeyama et al. |
| 2018/0086948 A1 | 3/2018 | Hatakeyama et al. |
| 2018/0168470 A1 | 6/2018 | Hatakeyama et al. |
| 2018/0223133 A1 | 8/2018 | Hatakeyama et al. |
| 2018/0229023 A1 | 8/2018 | Hatakeyama et al. |
| 2018/0229024 A1 | 8/2018 | Hatakeyama et al. |
| 2019/0117101 A1* | 4/2019 | Hatakeyama ...... C08G 18/3212 |
| 2019/0151648 A1 | 5/2019 | Hatakeyama et al. |
| 2019/0159978 A1 | 5/2019 | Sakuta et al. |
| 2019/0298891 A1 | 10/2019 | Hatakeyama et al. |
| 2020/0113464 A1 | 4/2020 | Hatakeyama et al. |
| 2020/0315476 A1 | 10/2020 | Hatakeyama et al. |
| 2020/0317840 A1 | 10/2020 | Hatakeyama et al. |

FOREIGN PATENT DOCUMENTS

| | | |
|---|---|---|
| JP | H05-095924 A | 4/1993 |
| JP | 2003-225217 A | 8/2003 |
| JP | 2004-33468 A | 2/2004 |
| JP | 2015-19806 A | 2/2015 |
| JP | 2015-100673 A | 6/2015 |
| JP | 2015-193803 A | 11/2015 |
| JP | 2018-44147 A | 3/2018 |
| JP | 2018-59050 A | 4/2018 |
| JP | 2018-59052 A | 4/2018 |
| JP | 2018-099504 A | 6/2018 |
| JP | 2018-126496 A | 8/2018 |
| JP | 2018-130533 A | 8/2018 |
| JP | 2018-130534 A | 8/2018 |
| JP | 2019-503406 A | 2/2019 |
| JP | 2019-99469 A | 6/2019 |
| JP | 2020-002342 A | 1/2020 |
| KR | 10-2020-0117878 A | 10/2020 |
| TW | 201927904 A | 7/2019 |
| TW | 201942210 A | 11/2019 |
| WO | 2013/039151 A1 | 3/2013 |

OTHER PUBLICATIONS

Komaba, Impact of Sodium Salt Coating on a Graphite Negative Electrode for Lithium-Ion Batteries, Electrochemical and Solid-State Letters, 2006, 9 (3), A130-A133 (Year: 2010).*
Mar. 18, 2022 Extended Search Report issued in European Patent Application No. 21206005.7.
Oct. 11, 2023 Office Action issued in Korean Patent Application No. 10-2021-0148767.
Feb. 24, 2023 Office Action and Search Report issued in Taiwanese Patent Application No. 110140859.
Mar. 29, 2024 Office Action Issued in Chinese Patent Application No. 202111299558.0.

* cited by examiner

[FIG. 1]
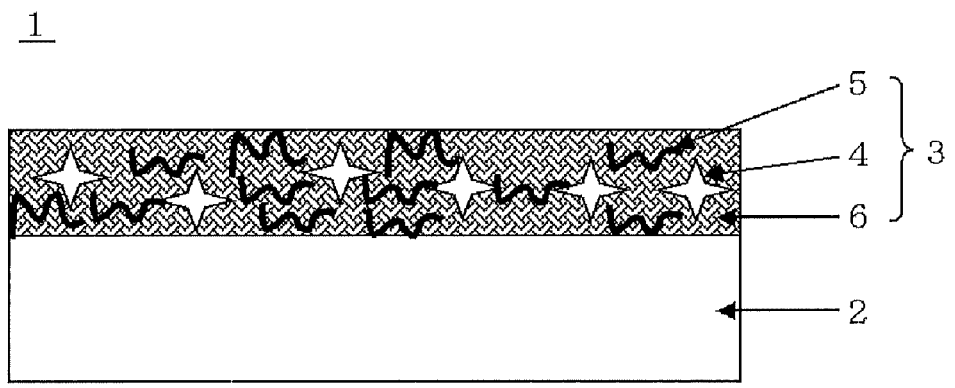
[FIG. 2]
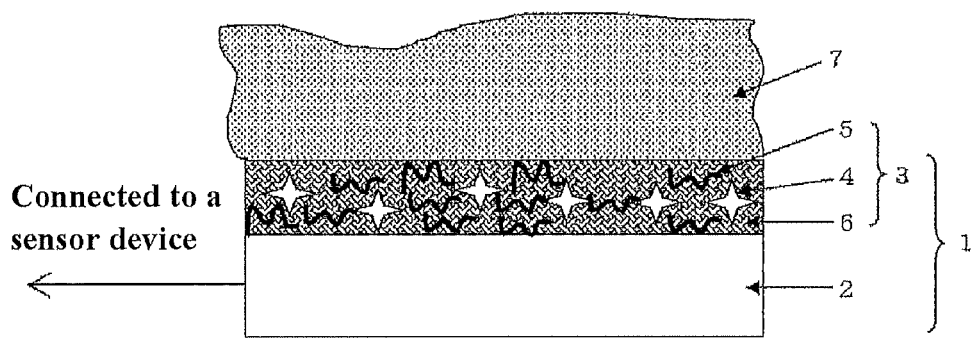
Connected to a sensor device
[FIG. 3]
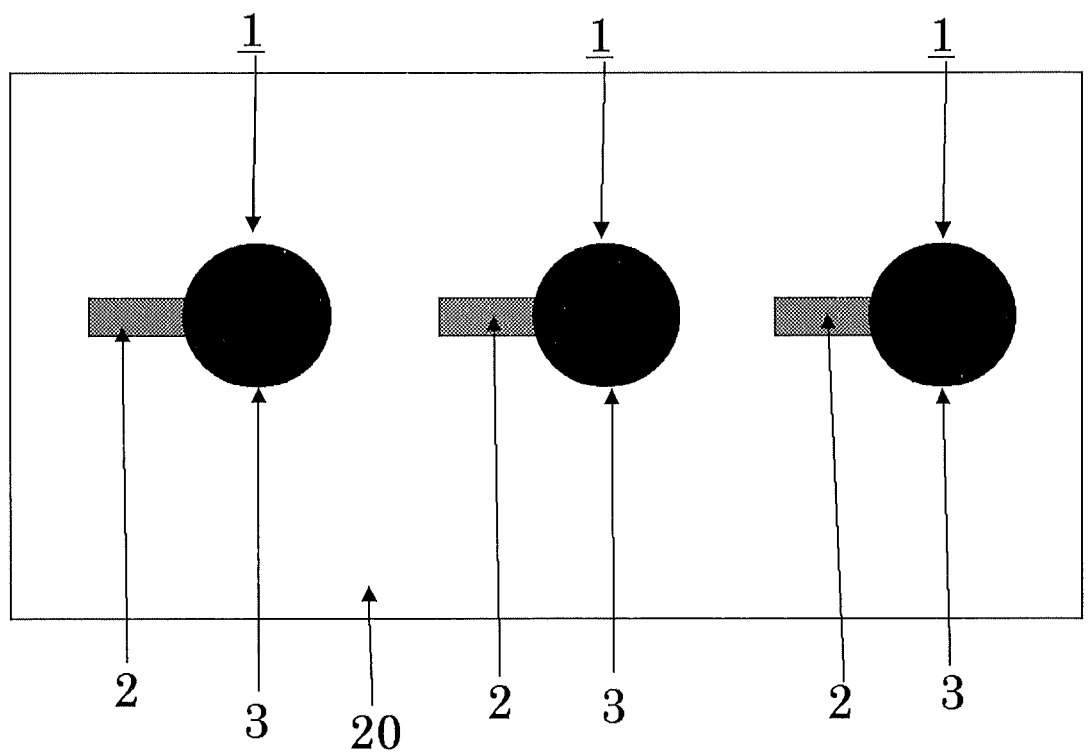

[FIG. 4]
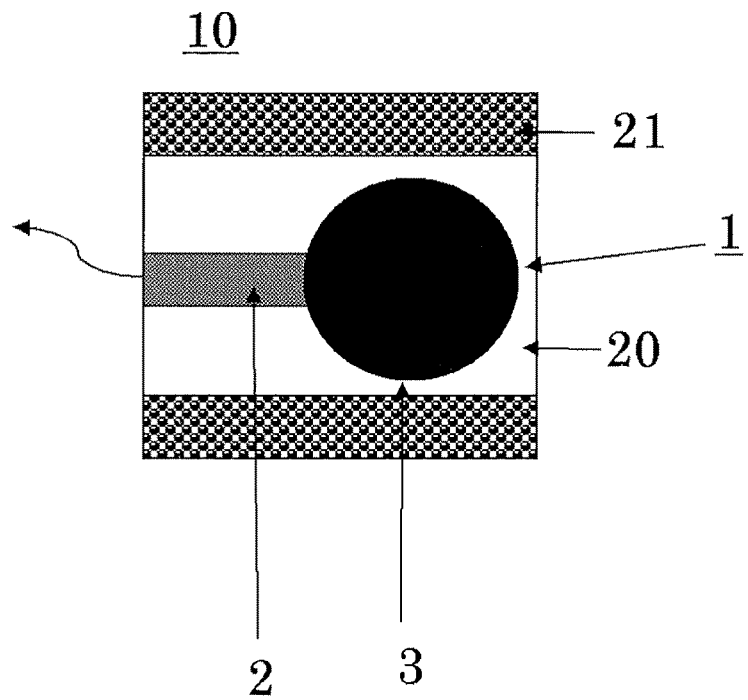
[FIG. 5]
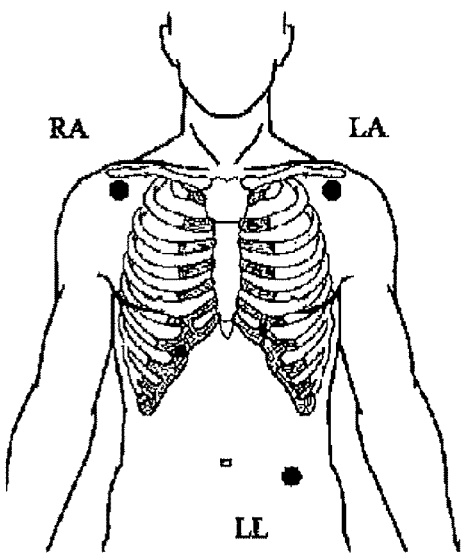
[FIG. 6]

BIO-ELECTRODE COMPOSITION, BIO-ELECTRODE, AND METHOD FOR MANUFACTURING BIO-ELECTRODE

TECHNICAL FIELD

The present invention relates to a bio-electrode that is used in contact with the skin of a living body and capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of wearable devices, such as watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detects an electric signal to measure the motion of the heart. The electrocardiogram measurement is conducted by attaching an electrode coated with an electro-conductive paste to a body, but this is a single (not continuous), short-time measurement. On the other hand, the above medical wearable device is aimed at continuously monitoring the health condition for a few days. Accordingly, a bio-electrode used in a medical wearable device is required to make no changes in electric conductivity even in long-time use and cause no skin allergy. In addition to these, it is also required that a bio-electrode is light-weight and can be produced at low cost.

To prevent medical collapse by the global pandemic of novel coronavirus and by the accompanying hospitalization of many virus-infected patients that exceed the capacity of hospitals, the importance of home medical care is recognized. There has been proposed online clinical practice (telehealth) that allows a doctor in a hospital to diagnose the health condition of a person at home. For this purpose, the development of an inexpensive and highly-precise wearable device has been demanded.

Medical wearable devices are classified into two types: a type which is directly attached to body and a type which is incorporated into clothes. As the type which is attached to a body, it has been proposed a bio-electrode using water-soluble gel containing water and electrolyte, which are materials of the foregoing electro-conductive paste (Patent Document 1). The water-soluble gel contains sodium, potassium, or calcium as the electrolyte in a water-soluble polymer for retaining water, and converts changes of ion concentration from skin into electricity. On the other hand, as the type which is incorporated into clothes, it has been proposed a means to use cloth in which an electro-conductive polymer such as PEDOT-PSS (poly-3,4-ethylenedioxy-thiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of excessive polystyrenesulfonic acid not used in the doping with the electro-conductive polymer, and further cause peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. The carbon nanotubes can stimulate (irritate) a living body by the same reason. Although the carbon black is not as poisonous as carbon nanotube, it also stimulates the skin to a certain degree. Even if these electrode materials themselves cause no allergic reaction in the manners described above, the biocompatibility may be degraded depending on the shape of a material and its inherent stimulation, thereby making it hard to satisfy both electric conductivity and biocompatibility.

Although metal films seem to function as excellent bio-electrodes thanks to extremely high electric conductivity, this is not always the case. Upon heartbeat, the human skin releases not only extremely weak current, but also sodium ion, potassium ion, and calcium ion. It is thus necessary to convert changes in ion concentration into current. Noble metals, however, are difficult to ionize and are inefficient in converting ions from skin to current. Therefore, the resulting bio-electrode using the noble metal has high impedance and high resistance to the skin during electrical conduction.

There have been proposed bio-electrodes in each of which an ionic polymer is added (Patent Documents 6, 7, 8). A bio-electrode obtained by mixing a silicone adhesive with an ionic polymer and a carbon powder added thereto has adhesion and high water repellency so that biological signals can be stably collected even when the bio-electrode is attached to the skin for a long time during which the user takes a shower and sweat. Ion polymers do not permeate the skin and hence do not stimulate the skin, and the biocompatibility is high. From these aspects, the bio-electrode enables long-time attachment.

Although silicones are inherently insulators, the ionic conductivity is improved by the combination with an ion polymer and a carbon powder, and thus the function as a bio-electrode is obtained. Nevertheless, it has been desired to improve the performance by further improving the ionic conductivity.

Printable electronics, by which devices are fabricated through printing, has attracted attention. If devices for living body can be produced by roll-to-roll printing, cost reduction is achieved by the productivity improvement. Printable electronics is also characterized by enabling light-weight thin films. To ease the wearing feeling upon attachment to skin, characteristics of being light, thin, short, and small are important.

When peeled after attachment on skin for a few days, wearable devices should not leave any residue on the skin. Particularly, bio-electrodes are required to have not only sufficient adhesion for the attachment on skin but also sufficient film strength for the prevention of residue after the peeling.

To produce bio-electrodes by printing, time margin is necessary from ink preparation for printing a bio-electrode to printing, or from the printing to baking for film solidification. Without this time margin, no spare time is available between the ink preparation and the printing, for example.

Strict time management is required, and no appropriate action can be taken when the printing machine is stopped due to sudden trouble. For stable production by printing, a material is required to provide spare time from ink preparation to printing and then to film curing.

CITATION LIST

Patent Literature

Patent Document 1: WO 2013/039151 A1
Patent Document 2: JP 2015-100673 A
Patent Document 3: JP H05-095924 A
Patent Document 4: JP 2003-225217 A
Patent Document 5: JP 2015-019806 A
Patent Document 6: JP 2018-99504 A
Patent Document 7: JP 2018-126496 A
Patent Document 8: JP 2018-130533 A

SUMMARY OF INVENTION

Technical Problem

The present invention has been made to solve the above problems. An object of the present invention is to provide: a bio-electrode composition capable of forming a living body contact layer for a bio-electrode which is excellent in electric conductivity and biocompatibility, light-weight, and manufacturable at low cost, and which does not leave residue on skin after attachment to and peeling from the skin; a bio-electrode including a living body contact layer formed of the bio-electrode composition; and a method for manufacturing the bio-electrode.

Solution to Problem

To achieve the object, the present invention proposes the following bio-electrode composition and bio-electrode.

Specifically, the present invention provides a bio-electrode composition comprising:
(A) an ionic polymer material;
(B) an addition reaction-curable silicone having at least a hydrosilyl group;
(C) a platinum-group catalyst; and
a solvent, wherein
the bio-electrode composition has a water content of 0.2 mass % or less, and
the solvent comprises one or more of an ether solvent, an ester solvent, and a ketone solvent each of which does not contain a hydroxy group, a carboxyl group, a nitrogen atom, or a thiol group.

The inventive bio-electrode composition is capable of forming a living body contact layer for a bio-electrode which is excellent in electric conductivity and biocompatibility, light-weight, and manufacturable at low cost, and which does not leave residue on skin after attachment to and peeling from the skin.

The bio-electrode composition may be a mixture of:
a solution containing the ionic polymer material as the component (A);
the addition reaction-curable silicone having at least a hydrosilyl group as the component (B); and
a solution containing the platinum-group catalyst as the component (C), and
the component (A) and the component (B) each have a water content of 0.2 mass % or less.

In such a bio-electrode composition, the water content in each of the components (A) and (B) is so low that the deactivation reaction of the hydrosilyl group does not proceed immediately after the components (A) and (B) are mixed. Even when a bio-electrode is formed after the mixture of the components (A), (B), and (C) is left standing, biological signals are collected from this bio-electrode having been attached to skin, and no residue remains on the skin after the bio-electrode is then peeled therefrom.

In this case, a solvent of the solution of the component (A) can be one or more of an ether solvent, an ester solvent, and a ketone solvent each of which does not contain a hydroxy group, a carboxyl group, a nitrogen atom, or a thiol group, and the component (B) can be solvent-free or a solution with a hydrocarbon solvent or an ether solvent.

The ionic polymer material of the component (A) has a high polarity and is hence easily dissolved in such one or more of ether solvent, ester solvent, and ketone solvent as described above. An organosilicone having a hydrosilyl group like the component (B) is easily dissolved in a hydrocarbon solvent or an ether solvent (the component (B) may be free of solvent). When the component (A) is to be mixed with the component (B), the mixing can be carried out quickly by dissolving the ionic polymer compound (polymer material) in the solvent in advance.

More preferably, in the inventive bio-electrode composition, the ionic polymer material of the component (A) is a polymer compound comprising a repeating unit having a structure selected from the group consisting of salts of a sodium, a potassium, and a silver of one or more of fluorosulfonic acid, fluorosulfonimide, and N-carbonyl-fluorosulfonamide.

Such bio-electrode compositions can suitably form a living body contact layer for a bio-electrode which is excellent in electric conductivity and biocompatibility, light-weight, and manufacturable at low cost, and which prevents significant reduction in the electric conductivity even when the bio-electrode is wetted with water or dried.

In this case, the structure is preferably shown by any of the following general formulae (1)-1 to (1)-4,

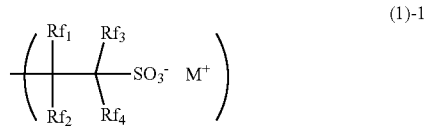

(1)-1

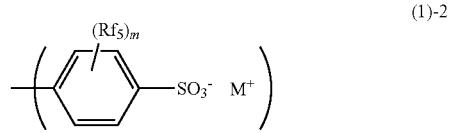

(1)-2

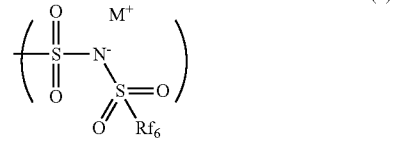

(1)-3

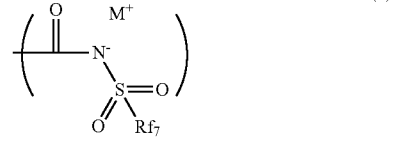

(1)-4 wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that at least one of $R_1$ to $Rf_4$ is a fluorine atom or a trifluoromethyl group; $Rf_5$, $Rf_6$, and $Rf_7$ each represent a fluorine atom, a linear alkyl group having 1 to 4 carbon atoms, or a branched alkyl group having 3 or 4 carbon atoms, and have at least one fluorine atom; "m" represents an integer of 1 to 4; and M represents sodium, potassium, or silver.

Such a bio-electrode composition can further enhance the effects of the present invention.

Further preferably, one or more repeating units having structures selected from the group consisting of salts of a sodium, a potassium, and a silver of fluorosulfonic acid shown by the general formula (1)-1 or (1)-2, sulfonimide shown by (1)-3, or sulfonamide shown by (1)-4 comprise at least one repeating unit selected from the group consisting of repeating units-a1 to -a7 shown by the following general formula (2),

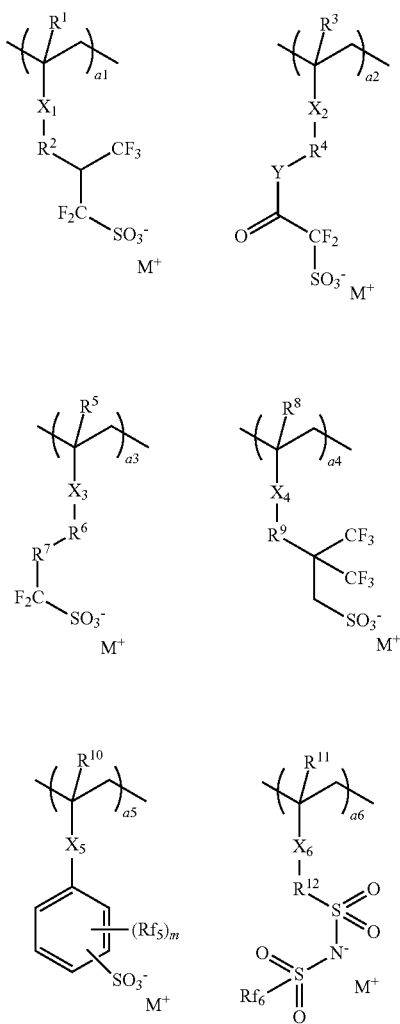

(2)

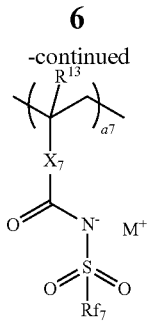

wherein $R^1$, $R^3$, $R^5$, $R^8$, $R^{10}$ or $R^{11}$, and $R^{13}$ each independently represent a hydrogen atom or a methyl group; $R^2$, $R^4$, $R^6$, $R^9$, and $R^{12}$ each independently represent any of a single bond, an ester group, a linear divalent hydrocarbon group having 1 to 13 carbon atoms, and a branched or cyclic divalent hydrocarbon group having 3 to 12 carbon atoms, the divalent hydrocarbon groups optionally having either or both of an ether group and an ester group; $R^7$ represents a linear alkylene group having 1 to 4 carbon atoms or a branched alkylene group having 3 to 12 carbon atoms, and one or two hydrogen atoms in $R^7$ are optionally substituted with a fluorine atom; $X_1$, $X_2$, $X_3$, $X_4$, and $X_6$ each independently represent any of a single bond, a phenylene group, a naphthylene group, an ether group, an ester group, and an amide group; $X_5$ represents any of a single bond, an ether group, and an ester group; $X_7$ represents a single bond, an arylene group having 6 to 12 carbon atoms, or —C(=)—O—$X_{10}$—; $X_{10}$ represents a linear, branched, or cyclic alkylene group having 1 to 12 carbon atoms, or a divalent aromatic hydrocarbon group having 6 to 10 carbon atoms, and $X_{10}$ optionally contains an ether group, a carbonyl group, or an ester group; Y represents an oxygen atom or a —$NR^{19}$— group, optionally bonded to $R^4$ to form a ring; $R^{19}$ represents a hydrogen atom, a linear alkyl group having 1 to 4 carbon atoms, or a branched alkyl group having 3 or 4 carbon atoms; "m" represents an integer of 1 to 4; a1, a2, a3, a4, a5, a6, and a7 represent numbers satisfying $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; and M, $Rf_5$, $Rf_6$, and $Rf_7$ are as defined above.

Such a bio-electrode composition can achieve still further enhancement of the effects of the present invention.

Additionally, in the present invention, the component (B) may comprise organopolysiloxane having a hydrosilyl group.

The component (B) may comprise organopolysiloxane having a hydrosilyl group and diorganopolysiloxane having an alkenyl group.

In the inventive bio-electrode composition, such components (B) can be suitably used.

The component (B) may further comprise a silicone resin having an $SiO_2$ unit and an $R_xSiO_{(4-x)/2}$ unit, wherein
  R represents a substituted or unsubstituted monovalent hydrocarbon group having 1 to 10 carbon atoms, and
  "x" represents a number in a range of 2.5 to 3.5.

Incorporating such a component (B) enhances the adhesive strength.

Moreover, in the present invention, the component (A) can comprise diorganosiloxane having an alkenyl group in addition to the ionic polymer material.

In the inventive bio-electrode composition, such a component (A) is suitably usable.

The component (A) may further comprise a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

Incorporating such a component (A) enhances the adhesive strength.

Moreover, the present invention may further comprise a component (D) in the component (A) or (B), the component (D) being one or more selected from the group consisting of carbon powder, metal powder, silicon powder, lithium titanate powder, and metal chloride powder.

By further adding such electro-conductive powder(s) (carbon powder, metal powder, silicon powder, lithium titanate powder, metal chloride powder), the electric conductivity can be enhanced even more.

In this case, the carbon powder is preferably any of carbon black, graphite, and carbon nanotube, or a combination thereof, and can further comprise an ion component, too.

Such materials can furthermore enhance the electric conductivity.

The metal powder is preferably a powder of a metal selected from the group consisting of gold, silver, platinum, copper, tin, titanium, nickel, aluminum, tungsten, molybdenum, ruthenium, chromium, and indium, particularly preferably a silver powder.

Such materials can increase the electron conductivity.

The present invention also provides a method for producing the above-described bio-electrode composition, comprising:

storing (A) the ionic polymer material, (B) the addition reaction-curable silicone having at least a hydrosilyl group, and (C) the platinum-group catalyst in separate containers; and mixing these components to produce a bio-electrode composition when a bio-electrode is manufactured.

The inventive method for producing the bio-electrode composition enables efficient and low-cost production of a bio-electrode composition capable of forming a living body contact layer for a bio-electrode which is excellent in electric conductivity and biocompatibility, and light-weight, and which does not leave residue on skin after the attachment and peeling from the skin.

In a method for producing the bio-electrode composition according to the present invention, the component (D) may mix into the component (A) or (B) before or at the same time when blending the component (C).

Such a method for producing the bio-electrode composition can minimize the influence of water derived from the component (D).

Moreover, the present invention provides a bio-electrode comprising an electro-conductive base material and a living body contact layer formed on the electro-conductive base material, wherein the living body contact layer is a cured product of the above-described bio-electrode composition.

The inventive bio-electrode is excellent in electric conductivity and biocompatibility, and light-weight, and does not leave residue on skin after attachment to and peeling from the skin.

In this case, the electro-conductive base material preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the present invention, such electro-conductive base materials are suitably usable.

Further, the present invention provides a method for manufacturing a bio-electrode having an electro-conductive base material and a living body contact layer formed on the electro-conductive base material, comprising:

applying the above-described bio-electrode composition onto the electro-conductive base material; and curing the bio-electrode composition to form the living body contact layer.

The inventive method for manufacturing a bio-electrode enables efficient and low-cost manufacturing of a bio-electrode which is excellent in electric conductivity and biocompatibility, and light-weight, and which does not leave residue on skin after the attachment and peeling from the skin.

In this case, the electro-conductive base material preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the present invention, such electro-conductive base materials are suitably usable.

Advantageous Effects of Invention

As described above, the inventive bio-electrode composition contains: (A) an ionic polymer material; (B) an addition reaction-curable silicone having at least a hydrosilyl group; (C) a platinum-group catalyst; and a solvent. The water content of the bio-electrode composition is 0.2 mass % or less, and the solvent includes one or more of an ether solvent, an ester solvent, and a ketone solvent, but these solvents do not contain any of a hydroxy group, a carboxyl group, a nitrogen atom, and a thiol group. Such a bio-electrode composition enables the resulting film to be cured without inhibiting the addition reaction during the mixing of the components (A) to (C), applying, and baking. Moreover, the film has sufficient film strength, and leaves no residue on skin after peeling of the bio-electrode having been attached to the skin for biological signal measurement. Even if the time from the mixing of (A) to (C) to printing or the time from the printing to the baking is extended, the sufficient film strength is satisfactorily retained and no residue remains after the peeling. The deterioration due to long-term storage is avoided by placing the components (A) to (C) in different containers.

Moreover, the inventive bio-electrode has sufficient adhesion, keeps the contact area with skin constant, and is capable of detecting electric signals from skin stably with high sensitivity.

Further, the inventive method for manufacturing a bio-electrode enables simple, low-cost, and printing-based manufacturing of the inventive bio-electrode which is excellent in electric conductivity and biocompatibility, and light-weight, and which prevents significant reduction in the electric conductivity even when the bio-electrode is wetted with water or dried.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer thereon;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As noted above, it has been desired to develop: a bio-electrode composition that can form a living body contact layer for a bio-electrode which is excellent in electric conductivity and biocompatibility, light-weight, and manufacturable at low cost, and which prevents residue from remaining on skin after attachment to and peeling from the skin; a bio-electrode including a living body contact layer formed of the bio-electrode composition; and a method for manufacturing the bio-electrode.

The surface of skin releases extremely weak current and ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions.

The present inventors have noticed ionic liquids as a material that is highly ionic conductive. Ionic liquids are characterized by high thermal and chemical stability as well as excellent electric conductivity, thereby having been widely used for battery applications. Known ionic liquids include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium; etc. However, these salts (particularly, the ones with low molecular weight) are generally liable to hydrate, thereby resulting in such disadvantage that a salt is extracted with perspiration or by washing to lower the electric conductivity of a bio-electrode in which the living body contact layer is formed from any bio-electrode compositions containing these salts. In addition, the tetrafluoroborate salt is highly toxic, and the other salts are highly water-soluble to easily permeate into skin, thereby causing an issue of rough dry skin (i.e., highly irritative to skin).

In neutralized salts formed from highly acidic acids, the ions are strongly polarized to improve the ionic conductivity. This is why lithium salts of bis(trifluoromethanesulfonyl)imidic acid and tris(trifluoromethanesulfonyl)methide acid show high ionic conductivity in a lithium ion battery. On the other hand, the higher acidity of the acid before the neutral salt formation results in a problem that the salt has stronger irritation to a body. That is, ionic conductivity and irritation to a body are in relation of trade-off. However, a salt applied to a bio-electrode has to achieve both higher ionic conductivity and lower irritation to a body.

A salt compound decreases its permeability through skin and irritation to the skin as the molecular weight is larger or the structure is of higher order in three dimensions. Thus, the present inventors have conceived adding an ionic polymer compound to a bio-electrode composition.

Further, the present inventors have conceived that when this salt is mixed with an adhesive (resin), the use of this mixture enables constant adhesion to skin and stable electric-signal collection for a long term. The inventors have also conceived that silicone adhesive is preferably used as the adhesive from the viewpoints of biocompatibility, dermal respiration, and little skin deformation and little redness upon peeling.

Silicone adhesive is a hybrid of crosslinkable silicone and MQ resin. The crosslinking reaction thereof takes place by utilizing either radical crosslinking through peroxide breakdown, or hydrosilylation reaction between a hydrosilyl group and a vinyl group. Adding carbon into a bio-electrode composition is effective to enhance the electric conductivity. Nevertheless, since carbon absorbs radicals, carbon addition is disallowed in the case of radical crosslinking reaction. Meanwhile, as to the hydrosilylation reaction, carbon does not inhibit the reaction.

A hydrosilyl group reacts with water and a compound having an active proton, such as a hydroxy group-, a carboxyl group-, and a thiol group-containing compound. For example, when a hydrosilyl group reacts with water, a silanol group is formed, so that the hydrosilylation reaction with a vinyl group does not proceed. Accordingly, in order to make the hydrosilylation reaction proceed, the water content has to be lowered, and a compound which has a group containing an active proton, such as a hydroxy group, a carboxyl group, and a thiol group, should not be added as the solvent.

Water is likely to be incorporated into a solution containing an ionic polymer compound (polymer material) (also referred to as (A)-component or (A)-solution) but not a silicone having a hydrosilyl group ((B)-component or (B)-solution). The water contained in the (A)-solution causes deactivation reaction of the hydrosilyl group, when mixed with the (B)-solution. For this reason, the solution containing an ionic polymer compound of the (A)-component needs to be subjected to dehydration treatment. This dehydration treatment can be performed through azeotropic dehydration to increase the concentration of the solution containing an ionic polymer compound or with a dehydrator, such as molecular sieves.

The present inventors have earnestly studied the above problems, and consequently found that: lowering the water content in a bio-electrode composition as well as the content of a compound having an active proton-containing group, such as a hydroxy group, a carboxyl group, and a thiol group, suppresses the deactivation reaction of a hydrosilyl group mixed therewith and prevents the hydrosilylation reaction from being inhibited; and a bio-electrode formed from such a bio-electrode composition with less contents of water and the compound having an active proton does not leave residue on skin after attachment to and peeling from the skin. These findings have led to the completion of the present invention.

Specifically, the present invention provides a bio-electrode composition comprising:

(A) an ionic polymer material;
(B) an addition reaction-curable silicone having at least a hydrosilyl group;
(C) a platinum-group catalyst; and
a solvent, wherein
the bio-electrode composition has a water content of 0.2 mass % or less, and
the solvent comprises one or more of an ether solvent, an ester solvent, and a ketone solvent each of which does not contain a hydroxy group, a carboxyl group, a nitrogen atom, or a thiol group.

Hereinafter, the present invention will be described in detail, but the present invention is not limited thereto.

Note that, in the following description, the term component also means to include a solution containing the component.

<Bio-Electrode Composition>

The inventive bio-electrode composition is characterized as follows. Specifically, the bio-electrode composition contains (A) an ionic polymer material, (B) an addition reaction-curable silicone having at least a hydrosilyl group, (C) a platinum-group catalyst, and a solvent. The bio-electrode composition has a water content of 0.2 mass % or less. The solvent includes one or more of an ether solvent, an ester solvent, and a ketone solvent each of which does not contain a hydroxy group, a carboxyl group, a nitrogen atom, or a thiol group. As will be described later, the inventive bio-electrode composition can contain other components than the components (A) to (C), as necessary.

If the water content in the bio-electrode composition is so high that the water reacts with the hydrosilyl group of the silicone in the composition, a silanol group is formed, and crosslinking attributable to hydrosilylation between the Si—H group and Si-vinyl group or the like in the presence of the platinum-group catalyst does not proceed. If the crosslinking reaction does not proceed, the resulting film strength is weakened, and in-film fracture occurs when the bio-electrode is attached and peeled, so that a residue of the bio-electrode is left on the skin.

Particularly, in a case where the bio-electrode composition is a mixture including a solution containing (A) an ionic polymer material, (B) an addition reaction-curable silicone, and a solution containing (C) a platinum-group catalyst, if the water content in each solution of the components (A) and (B) exceeds 0.2 mass %, the hydrosilyl group of the silicone of the component (B) in the mixture reacts with water to form a silanol group, so that the above-described trend is more noticeable.

Additionally, if the solution containing (A) an ionic polymer material in which a solvent contains a hydroxy group, a carboxyl group, a nitrogen atom, or a thiol group, the solvent reacts with the hydrosilyl group, so that the ratio of the hydrosilyl group is lowered, and the hydrosilylation reaction is inhibited. Because of the high polarity, the ionic polymer material is easily dissolved into a solvent containing a hydroxy group, a carboxyl group, a nitrogen atom, or a thiol group. Thus, the ionic polymer material (A) needs to be dissolved in an ether solvent, an ester solvent, or a ketone solvent each of which does not contain these moieties.

Accordingly, it is essential that the inventive bio-electrode composition should have a water content of 0.2 mass % or less, and that the solvent thereof should include one or more of an ether solvent, an ester solvent, and a ketone solvent each of which does not contain a hydroxy group, a carboxyl group, a nitrogen atom, or a thiol group. Note that the water contents in the solvents, the solutions, and the bio-electrode composition can be measured by Karl Fischer method.

Hereinbelow, the inventive bio-electrode composition will be described in detail.

[Component (A)]

The component (A) is an ionic polymer material. Silicones are inherently insulators, but the ionic conductivity is enhanced depending on the combination with an ionic polymer (ionic polymer material), and thereby the function as a bio-electrode is demonstrated. The ionic polymer material is not particularly limited, as long as it has ionic conductivity.

The ionic polymer material is preferably a polymer compound containing a repeating unit having a structure selected from the group consisting of salts of a sodium, a potassium, and a silver of one or more of fluorosulfonic acid, fluorosulfonimide, and N-carbonyl-fluorosulfonamide.

The bio-electrode compositions containing such ionic polymer compounds can suitably form a living body contact layer for a bio-electrode which is excellent in electric conductivity and biocompatibility, light-weight, and manufacturable at low cost, and which prevents significant reduction in the electric conductivity even when the bio-electrode is wetted with water or dried.

More preferably, the ionic repeating units having the structures are shown by any of the following general formulae (1)-1 to (1)-4.

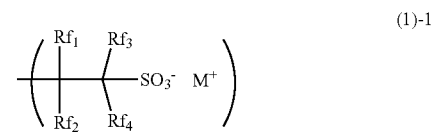

(1)-1

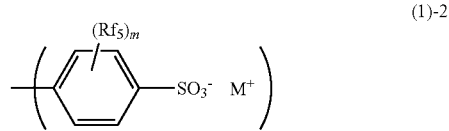

(1)-2

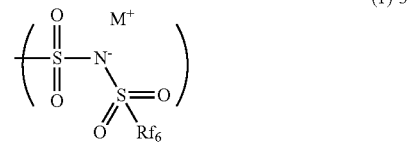

(1)-3

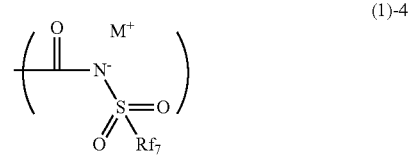

(1)-4

In the formulae, $Rf_1$ and $Rf_2$ each represent a hydrogen atom, a fluorine atom, an oxygen atom, a methyl group, or a trifluoromethyl group. When $Rf_1$ represents an oxygen atom, $Rf_2$ also represents the oxygen atom to form a carbonyl group together with a carbon atom bonded with $Rf_1$ and $Rf_2$. $Rf_2$ and $Rf_4$ each represent a hydrogen atom, a fluorine atom, or a trifluoromethyl group. At least one of $Rf_1$ to $Rf_4$ is a fluorine atom or a trifluoromethyl group. $Rf_5$, $Rf_6$, and $Rf_7$ each represent a fluorine atom, a linear alkyl group having 1 to 4 carbon atoms, or a branched alkyl group having 3 or 4 carbon atoms, and have at least one fluorine atom. "m" represents an integer of 1 to 4. M represents sodium, potassium, or silver.

Furthermore preferably, the ionic repeating units are selected from the group consisting of a1 to a7 in the following general formula (2).

(2)

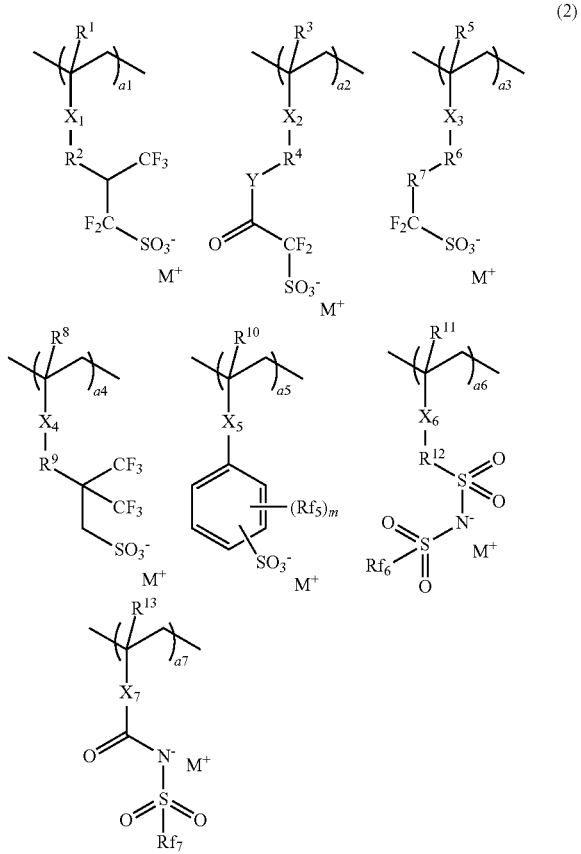

In the formula, $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent any of a single bond, an ester group, a linear divalent hydrocarbon group having 1 to 13 carbon atoms, and a branched or cyclic divalent hydrocarbon group having 3 to 12 carbon atoms. The divalent hydrocarbon groups optionally have either or both of an ether group and an ester group. $R^7$ represents a linear alkylene group having 1 to 4 carbon atoms or a branched alkylene group having 3 to 12 carbon atoms. One or two hydrogen atoms in $R^7$ are optionally substituted with a fluorine atom. $X_1$, $X_2$, $X_3$, $X_4$, and $X_6$ each independently represent any of a single bond, a phenylene group, a naphthylene group, an ether group, an ester group, and an amide group. $X_5$ represents any of a single bond, an ether group, and an ester group. $X_7$ represents a single bond, an arylene group having 6 to 12 carbon atoms, or —C(=O)—O—$X_{10}$—. $X_{10}$ represents a linear, branched, or cyclic alkylene group having 1 to 12 carbon atoms, or a divalent aromatic hydrocarbon group having 6 to 10 carbon atoms. $X_{10}$ optionally contains an ether group, a carbonyl group, or an ester group. Y represents an oxygen atom or a —$NR^{19}$— group. Y is optionally bonded to $R^4$ to form a ring. $R^{19}$ represents a hydrogen atom, a linear alkyl group having 1 to 4 carbon atoms, or a branched alkyl group having 3 or 4 carbon atoms. "m" represents an integer of 1 to 4. a1, a2, a3, a4, a5, a6, and a7 represent numbers (defining mole fractions) satisfying $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$. M, $Rf_5$, $Rf_6$, and $Rf_7$ are as defined above.

Monomers for obtaining the ionic repeating units selected from a1 to a7 in the general formula (2) are specifically disclosed in paragraphs [0061] to [0091] of JP 2020-002342 A. Monomers copolymerized therewith, copolymerization ratios, polymerization methods, molecular weights, etc. disclosed in paragraphs [0112] to [0135] can be adopted herein.

When such an ionic polymer compound is to be mixed with an organosilicone having a hydrosilyl group, the mixing can be facilitated by dissolving the ionic polymer compound in a solvent in advance. As the solvent in which the ionic polymer compound is dissolved, it is preferable to use an ether solvent, an ester solvent, or a ketone solvent each of which has a water content of 0.2 mass % or less and does not have an active proton-containing group, such as a hydroxy group, a carboxyl group, or a thiol group.

Examples of the ether solvent for dissolving the ionic polymer compound include ethylene glycol dimethyl ether, ethylene glycol diethyl ether, ethylene glycol dipropyl ether, ethylene glycol methyl butyl ether, ethylene glycol dibutyl ether, propylene glycol dimethyl ether, propylene glycol diethyl ether, propylene glycol dipropyl ether, propylene glycol dibutyl ether, propylene glycol methyl propyl ether, propylene glycol methyl butyl ether, diethylene glycol dimethyl ether, diethylene glycol methyl ethyl ether, diethylene glycol diethyl ether, diethylene glycol divinyl ether, diethylene glycol diallyl ether, diethylene glycol dipropyl ether, diethylene glycol isopropyl methyl ether, diethylene glycol dibutyl ether, diethylene glycol methyl butyl ether, diethylene glycol methyl phenyl ether, diethylene glycol methyl benzyl ether, diethylene glycol bis(2-propynyl)ether. Specific examples of the ketone solvent include cyclopentanone, 2-carbonyl ethoxy cyclopentanone, 2-methoxy carbonyl cyclopentanone, 2-ethoxy carbonyl cyclopentanone, 2-heptylcyclopentanone, 2,2,4-trimethylcyclopentanone, 2-cyclopentylcyclopentanone, 2-acetylcyclopentanone, 2-cyclopenten-1-one, 3-methyl-2-cyclopentenone, 2-pentyl-2-cyclopenten-1-one, 2-amyl-3-methyl-2-cyclopenten-1-one, cyclohexanone, 3,3,5-trimethylcyclohexanone, 4,4-dimethylcyclohexanone, 2-methoxycyclohexanone, 2-propylcyclohexanone, 4-propylcyclohexanone, 3,4-dimethylcyclohexanone, 3,3-dimethylcyclohexanone, 2-cyclohexylcyclohexanone, 2-allylcyclohexanone, 2-methylcyclohexanone, 3-methylcyclohexanone, 4-methylcyclohexanone, 4-tert-butylcyclohexanone, 2-acetylcyclohexanone, 4,4,dimethylcyclohexanone, 3,5-dimethylcyclohexanone, 4-ethylcyclohexanone, 2-sec-butylcyclohexanone, 2-cyclohexen-1-one, 3-methyl-2-cyclohexen-1-one, 4,4-dimethyl-2-cyclohexen-1-one, 3,5,5-trimethyl-2-cyclohexen-1-one, cycloheptanone, 2-octanone, 2-nonanone, 2-heptanone, 3-heptanone, 4-heptanone, 2-hexanone, 3-hexanone, diisobutyl ketone, methylcyclopentanone, methyl n-pentyl ketone, acetophenone, methylacetophenone, propiophenone, and isobutyrophenone.

Examples of the ester solvent include propylene glycol monomethyl ether acetate, propylene glycol monoethyl ether acetate, propylene glycol monopropyl ether acetate, propylene glycol monobutyl ether acetate, diethylene glycol monomethyl ether acetate, diethylene glycol monoethyl ether acetate, diethylene glycol monopropyl ether acetate, diethylene glycol monobutyl ether acetate, diethylene glycol diacetate, diethylene glycol monoethyl ether acrylate, diethylene glycol monomethyl ether methacrylate, diethylene glycol diacrylate, diethylene glycol dimethacrylate, ethyl pyruvate, butyl acetate, pentyl acetate, hexyl acetate, heptyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl 3-methoxypropionate, ethyl 3-ethoxypropionate, tert-butyl acetate, tert-butyl propionate, propylene glycol mono-tert-butyl ether acetate, methyl benzoate, ethyl benzoate, phenyl acetate, benzyl acetate, methyl phenylacetate, benzyl formate, phenyl ethyl formate, methyl 3-phenylpropionate, benzyl propionate, ethyl phenylacetate, acetic acid-2-phenylethyl ester, γ-butyrolactone, α-methyl-γ-butyrolactone, α-angelica lactone, δ-valerolactone, γ-valerolactone, β-methyl-γ-valerolactone, α-methylene-γ-butyrolactone, γ-methylene-γ-butyrolactone, γ-caprolactone, ε-caprolactone, γ-heptalactone, γ-octalactone, whisky lactone, γ-nonalactone, δ-nonalactone, etc.

[Component (B)]

The component (B) is an addition reaction-curable silicone having at least a hydrosilyl group, and is not particularly limited, as long as it has a hydrosilyl group and is cured by addition reaction.

The component (B) may serve as a matrix resin, or may be compatibilized (well mixed) with the component (A) to prevent elution of the salt, may function to hold an electric conductivity improver, if any, and exhibit adhesion.

The component (B) may contain organopolysiloxane having a hydrosilyl group, may contain diorganopolysiloxane having an alkenyl group in addition to the organopolysiloxane having a hydrosilyl group, or may further contain a silicone resin having an SiO$_2$ unit and an R$_x$SiO$_{(4-x)/2}$ unit, where R represents a substituted or unsubstituted monovalent hydrocarbon group having 1 to 10 carbon atoms, and "x" represents a number in a range of 2.5 to 3.5.

Examples of such components include ones containing diorganosiloxane having an alkenyl group, an MQ resin having R$_3$SiO$_{0.5}$ and SiO$_2$ units, and/or organohydrogenpolysiloxane having multiple SiH groups (hydrosilyl groups) described in JP 2015-193803A.

When the inventive bio-electrode composition is prepared, the solution component (A) containing an ionic polymer material is mixed with polysiloxane containing a hydrosilyl group as the component (B). Preferably, multiple hydrosilyl groups are present in each polysiloxane molecule.

To exhibit adhesion, a silicone resin having an SiO$_2$ unit and an R$_x$SiO$_{(4-x)/2}$ unit, where R represents a substituted or unsubstituted monovalent hydrocarbon group having 1 to 10 carbon atoms, and "x" represents a number in a range of 2.5 to 3.5, may be further added and incorporated into one or both of the components (A) and (B). It is preferable to mix diorganosiloxane having an alkenyl group and an MQ resin having R$_3$SiO$_{0.5}$ and SiO$_2$ units described in JP 2015-193803A.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength by addition of it, but does not bind to the polysiloxane in molecular level because it is not crosslinkable. The adhesive strength can be increased by integrating the polysiloxane and the resin as described above. Incorporating multiple alkenyl groups into the polysiloxane further increases the adhesive strength through the crosslinking reaction with the hydrosilyl groups.

[Solvent]

The inventive bio-electrode composition contains a solvent. The components may respectively contain solvents, and these may be the same as or different from one another. The solvent dissolves or disperses the components, and this can enhance the workability. However, some solvents contain water originally or by moisture absorption, for example. If such a solvent is used, the water content in the bio-electrode composition is increased. Consequently, the water reacts with the hydrosilyl group of the silicone in the composition to form a silanol group. This inhibits crosslinking attributable to the hydrosilylation between the Si—H group and Si-vinyl group or the like in the presence of a platinum-group catalyst. If no crosslinking reaction proceeds, the film strength is weakened. As a result, when the bio-electrode is attached and peeled, in-film fracture occurs and a residue of the bio-electrode is left on the skin.

Moreover, since the ionic polymer material has high polarity, this material easily dissolves into a solvent containing a hydroxy group, a carboxyl group, a nitrogen atom, or a thiol group. If such a solvent is used, active hydrogen in the solvent reacts with the hydrosilyl group. This lowers the proportion of the hydrosilyl group, and thereby inhibits the hydrosilylation reaction.

Thus, in view of enhancing the workability and suppressing the deactivation of the hydrosilyl group, the solvent in the present invention includes one or more of an ether solvent, an ester solvent, and a ketone solvent each of which is free from a hydroxy group, a carboxyl group, a nitrogen atom, or a thiol group. The solvent used in the present invention may further contain another solvent(s) as long as such specific solvent(s) are incorporated.

According to the inventive bio-electrode composition, the final water content in the entire composition is 0.2 mass % or less. As long as such a composition is formed, the water content of the solvent(s) to be employed may exceed 0.2 mass %. Nevertheless, from the viewpoint of suppressing the deactivation of the hydrosilyl group caused by water, each of the components (A) and (B) preferably has a water content of 0.2 mass % or less; more preferably, components other than the component (C) have a water content of 0.2 mass % or less. Note that the proportion of the platinum-group catalyst (C) blended relative to the entire composition is so small that even if the component (C) contains water, the water content in the final composition as a whole will be 0.2 mass % or less. Thus, water in the component (C) does not cause serious problem. The less the water content, the better. The water content may be, for example, in the range of 0.0001 to 0.2 mass %.

The solvent can be subjected to dehydration treatment in a conventional manner, for example, through azeotropic dehydration or with a dehydrator, such as molecular sieves. The dehydration treatment may be performed in advance or during the preparation of the composition.

In the inventive bio-electrode composition, a hydrocarbon-based organic solvent or ether-based organic solvent can be added in the component (B). Specific examples of the hydrocarbon-based organic solvent include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; and aliphatic hydrocarbon solvents, such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin. Examples of the isoparaffin-based solvent include ISOPAR C, ISOPAR E, ISOPAR G, ISOPAR H, ISOPAR L, ISOPAR M, and ISOPAR V (manufactured by Standard Sekiyu CO., LTD.).

Specific examples of the ether-based organic solvent include diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, anisole, 3-methoxytoluene, 4-methoxytoluene, trans-anethole, etc. From the viewpoint of suppressing the deactivation of the hydrosilyl group, the organic solvent may be a solvent which does not contain groups such as a hydroxy group, a carboxyl group, or a thiol group.

Note that the solvent is added in an amount preferably within 10 to 50,000 parts by mass relative to 100 parts by mass of the resin of the component (A) or (B).

[Component (C)]

The platinum-group catalyst of the component (C) enables crosslinking of diorganosiloxane having an alkenyl group and organohydrogenpolysiloxane having hydrosilyl groups by addition reaction.

Examples of the platinum-group catalyst of the component (C) include: platinum-based catalysts, such as chloroplatinic acid, alcohol solution of chloroplatinic acid, reaction product of chloroplatinic acid and alcohol, reaction product of chloroplatinic acid and an olefin compound, reaction product of chloroplatinic acid and vinyl group-containing siloxane, a platinum-olefin complex, and a complex of platinum and vinyl group-containing siloxane; platinum group metal-based catalysts, such as a rhodium complex and a ruthenium complex; etc. These catalysts may be used after dissolved or dispersed in alcohol solvent, hydrocarbon solvent, or siloxane solvent.

Note that the platinum-group catalyst can be added in an effective amount, preferably 5 to 2,000 ppm, particularly preferably 10 to 500 ppm, relative to 100 parts by mass of the resin.

The silicone-based resin can be improved in terms of compatibility with the foregoing salt by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple hydrosilyl groups.

Note that, as will be described later, the living body contact layer is a cured product of the bio-electrode composition. The curing improves the adhesion of the living body contact layer to both of skin and the electro-conductive base material.

When the addition-curable silicone resin is to be used, an addition-reaction inhibitor may be added in the component (A) or (B). This addition-reaction inhibitor is added as a quencher to prevent the action of the platinum-group catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The amount of the addition-reaction inhibitor added is not particularly limited, and is preferably within 0 to 10 parts by mass, particularly preferably 0.05 to 3 parts by mass, relative to 100 parts by mass of the resin.

[Component (D)]

The inventive bio-electrode composition can further contain an electro-conductive powder as a component (D). The electro-conductive powder is not particularly limited, as long as the powder has electric conductivity. The electro-conductive powder is preferably one or more selected from the group consisting of carbon powder (carbon material), metal powder, silicon powder, lithium titanate powder, and metal chloride powder, more preferably a carbon powder and/or a metal powder. The component (D) preferably mixes into the component (A) or (B) in advance. It is possible to further enhance the electric conductivity by further adding such electro-conductive powder(s) (carbon powder, metal powder, etc.). Note that, in the following description, the electro-conductive powder is also referred to as "electric conductivity improver".

[Carbon Powder]

As the electric conductivity improver, a carbon material (carbon powder) can be added. Examples of the carbon material include carbon black, graphite, carbon nanotube, carbon fiber, etc. The carbon nanotube may be either single layer or multilayer, and the surface may be modified with an organic group(s). The carbon powder may further contain an ion component. In other words, ions may be adsorbed onto the surface or incorporated into the inside of the carbon material (carbon powder). With ions adsorbed to or incorporated in the carbon material, the ionic conductivity is further enhanced, and the sensitivity to biological signals can be further increased. Examples of the method of adsorbing or incorporating ions onto or into the carbon powder can include: a method in which the carbon powder is dispersed in a solution containing ions and heated with stirring; and a method in which ions are implanted into the carbon powder. The carbon material is added in an amount preferably within 1 to 50 parts by mass relative to 100 parts by mass of the resin.

[Metal Powder]

To improve electron conductivity, the metal powder added as the component (D) to the inventive bio-electrode composition is preferably a powder of a metal selected from the group consisting of gold, silver, platinum, copper, tin, titanium, nickel, aluminum, tungsten, molybdenum, ruthenium, chromium, and indium. The amount of the metal powder added is not particularly limited, and is preferably within 1 to 50 parts by mass relative to 100 parts by mass of the resin.

As the kind of the metal powder, gold, silver, and platinum are preferable from the viewpoint of electric conductivity; and silver, copper, tin, titanium, nickel, aluminum, tungsten, molybdenum, ruthenium, and chromium are preferable from the viewpoint of cost. From the viewpoint of biocompatibility, noble metals are preferable. From comprehensive viewpoint including the above, silver is most preferable.

The metal powder may have any shape, such as a spherical shape, a disk shape, a flaky shape, and a needle shape. The addition of flaky powder brings highest electric conductivity and is preferable thereby. The metal powder is not particularly limited in terms of size, but is preferably a flake having relatively lower density and larger specific surface area with a size of 100 μm or less, a tapped density of not more than 5 g/cm$^3$, and a specific surface area of not less than 0.5 m$^2$/g. As the electric conductivity improver, both a metal powder and a carbon material (carbon powder) may be added.

[Silicon Powder]

The inventive bio-electrode composition may contain a silicon powder as the component (D) to enhance the ion reception sensitivity. Examples of the silicon powder include powders of silicon, silicon monoxide, or silicon carbide. The particle diameter of the powder is not particularly limited and is preferably smaller than 100 μm, more preferably 1 μm or less. Since finer particles have a larger surface area, the resulting bio-electrode can receive a larger amount of ions and has higher sensitivity. The amount of the silicon powder added is not particularly limited, and is preferably within 1 to 50 parts by mass relative to 100 parts by mass of the resin.

[Lithium Titanate Powder]

The inventive bio-electrode composition may contain a lithium titanate powder as the component (D) to enhance the ion reception sensitivity. Examples of the lithium titanate powder include powders containing a compound shown by molecular formula $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle diameter of the powder is not particularly limited and is preferably smaller than 100 μm, more preferably 1 μm or less. Since finer particles have a larger surface area, the bio-electrode can receive a larger amount of ions, and has higher sensitivity. These powders may be composite powders with carbon. The amount of the lithium titanate powder added is not particularly limited, and is preferably within 1 to 50 parts by mass relative to 100 parts by mass of the resin.

[Metal Chloride Powder]

The inventive bio-electrode composition may contain a metal chloride powder as the component (D) to enhance the ionic conductivity. Examples of the metal chloride powder include powders of alkali metal chlorides, such as sodium chloride and potassium chloride, and powders of alkaline earth metal chlorides, such as calcium chloride and magnesium chloride. Incidentally, these may also serve as ionic additives to be described later. Above all, sodium chloride and potassium chloride are preferable. The particle diameter of the powder is not particularly limited and is preferably smaller than 100 μm, more preferably 1 μm or less. Since finer particles have a larger surface area, such particles can more efficiently function as an ion carrier, and the resulting bio-electrode has higher sensitivity. These powders may be composite powders with carbon (i.e., a carbon powder further containing an ion component derived from a metal chloride). To incorporate a carbon powder, the aforementioned methods of incorporating an ion component into a carbon powder can be adopted. For example, an ion-treated carbon powder can be obtained by: adding a carbon powder such as graphite or carbon black into an aqueous solution of a metal chloride such as sodium chloride or potassium chloride or into an alcohol dispersion such as methanol dispersion; stirring the mixture with heating as necessary; and then evaporating the solvent (such as water, methanol). The amount of the metal chloride powder added is not particularly limited, and is preferably within 1 to 50 parts by mass relative to 100 parts by mass of the resin.

The particle diameter (size) of the metal powder and so forth can be a particle diameter (D50) which accounts for a cumulative value up to 50% in a volume-based particle size distribution determined by a laser diffraction scattering method. The measurement by laser diffraction scattering method can be performed, for example, with a particle size analyzer Microtrac MT3300EX (manufactured by Nikkiso Co., Ltd.).

[Component (E)]

The inventive bio-electrode composition can further contain a component (E), which is an additive, as necessary. Examples of the additive include moisture-holding components, such as polyether, polyglycerin, polyglycerin ester, polyether silicone, and polyglycerin silicone; and salts for enhancing the ionic conductivity, such as sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaine. Other examples include inorganic particles and silicone compound having a polyglycerin structure to be described later.

(Tackifier)

The bio-electrode composition may also contain a tackifier in order to have adhesion to a living body. Examples of such a tackifier include silicone resin, non-crosslinkable siloxane, non-crosslinkable poly(meth)acrylate, non-crosslinkable polyether, etc.

(Crosslinking Agent)

The bio-electrode composition may also contain an epoxy-type crosslinking agent. This crosslinking agent is a compound having multiple epoxy groups or oxetane groups in one molecule. The amount of the crosslinking agent added is preferably 1 to 30 parts by mass relative to 100 parts by mass of the resin.

(Crosslinking Catalyst)

The bio-electrode composition may also contain a catalyst for crosslinking the epoxy groups or the oxetane groups. As this catalyst, ones described in paragraphs [0027] to [0029] of JP 2019-503406A can be used. The amount of the catalyst added is preferably 0.01 to 10 parts by mass relative to 100 parts by mass of the resin.

(Ionic Additive)

The bio-electrode composition may contain an ionic additive to enhance the ionic conductivity. In consideration of biocompatibility, examples of the ionic additive include sodium chloride, potassium chloride, calcium chloride, saccharin sodium salt, acesulfame potassium, and salts disclosed in JP 2018-44147A, JP 2018-59050A, JP 2018-59052A, and JP 2018-130534A.

(Silicone Compound Having Polyglycerin Structure)

The inventive bio-electrode composition may also contain a silicone compound having a polyglycerin structure to enhance the sensitivity to ions released from skin and the ionic conductivity by enhancing the moisture-holding property of the film. The amount of the silicone compound having a polyglycerin structure blended is not particularly limited and is preferably 0.01 to 100 parts by mass, more preferably 0.5 to 60 parts by mass, relative to 100 parts by mass of a total of the components (A) and (B). Additionally, one kind of the silicone compound having a polyglycerin structure may be used alone, or two or more kinds thereof may be used in mixture.

The silicone compound having a polyglycerin structure is preferably shown by any of the following general formulae (4) and (5).

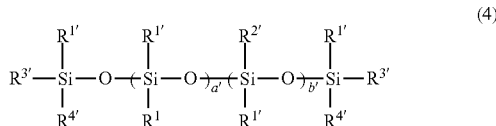

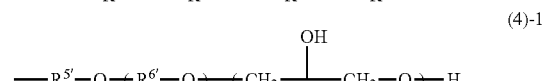

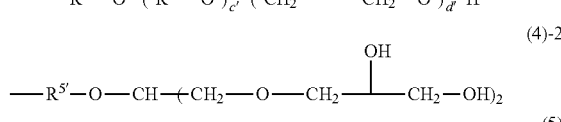

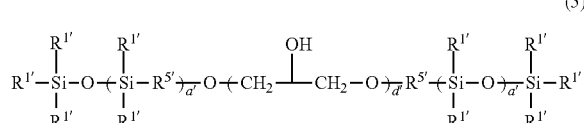

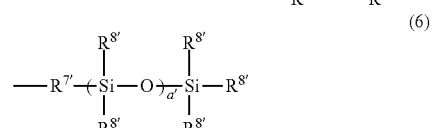

In the formulae (4) and (5), each $R^{1\prime}$ is identical to or different from one another, and independently represents a hydrogen atom, a phenyl group, a linear or branched alkyl group having 1 to 50 carbon atoms, or a silicone chain shown by a general formula (6), and optionally contains an ether group. $R^{2\prime}$ represents a group having a polyglycerin group structure shown by a formula (4)-1 or (4)-2. Each $R^{3\prime}$ is identical to or different from the other, and independently represents the $R^{1\prime}$ group or the $R^{2\prime}$ group. Each $R^{4\prime}$ is identical to or different from the other, and independently represents the $R^{1\prime}$ group, the $R^{2\prime}$ group, or an oxygen atom. When $R^{4\prime}$ represents an oxygen atom, the two $R^{4\prime}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3\prime}$ is the $R^{2\prime}$ group. In the formulae (4)-1, (4)-2 and (5), $R^{5\prime}$ represents an alkylene group having 2 to 10 carbon atoms or an aralkylene group having 7 to 10 carbon atoms. $R^{6\prime}$ and $R^{7\prime}$ each represent an alkylene group having 2 to 6 carbon atoms, but $R^{7\prime}$ may represent an ether bond. c' represents 0 to 20. d' represents 1 to 20. $R^{8\prime}$ represents a hydrogen atom, a linear or branched alkyl group having 1 to 50 carbon atoms and optionally containing an ether group, or a phenyl group.

Examples of such a silicone compound having a polyglycerin structure can include the following.

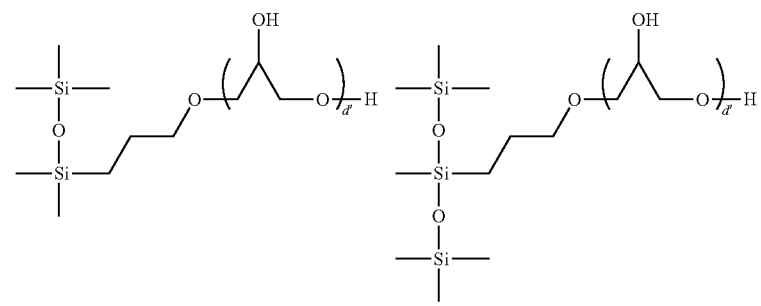

-continued
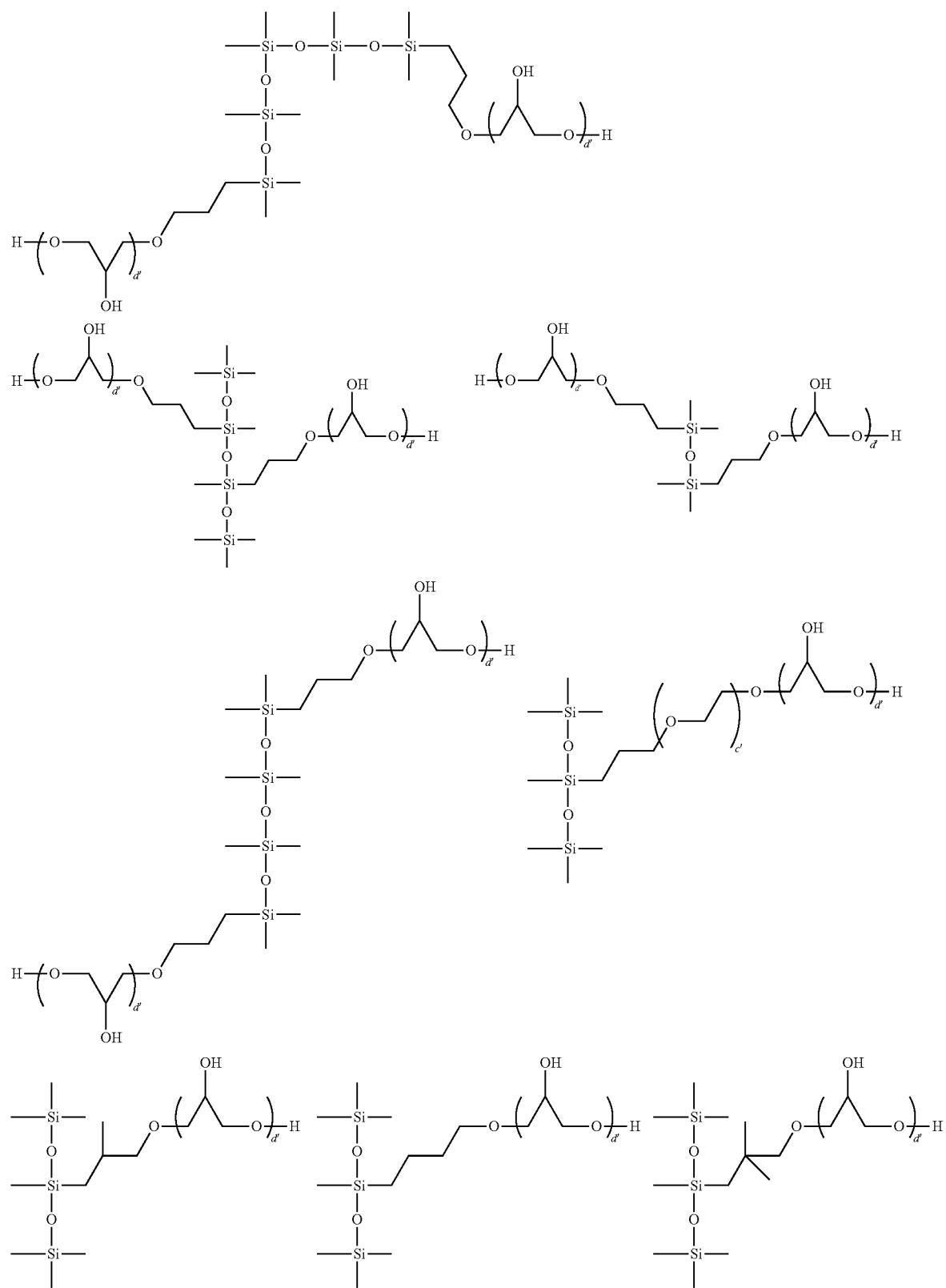

-continued
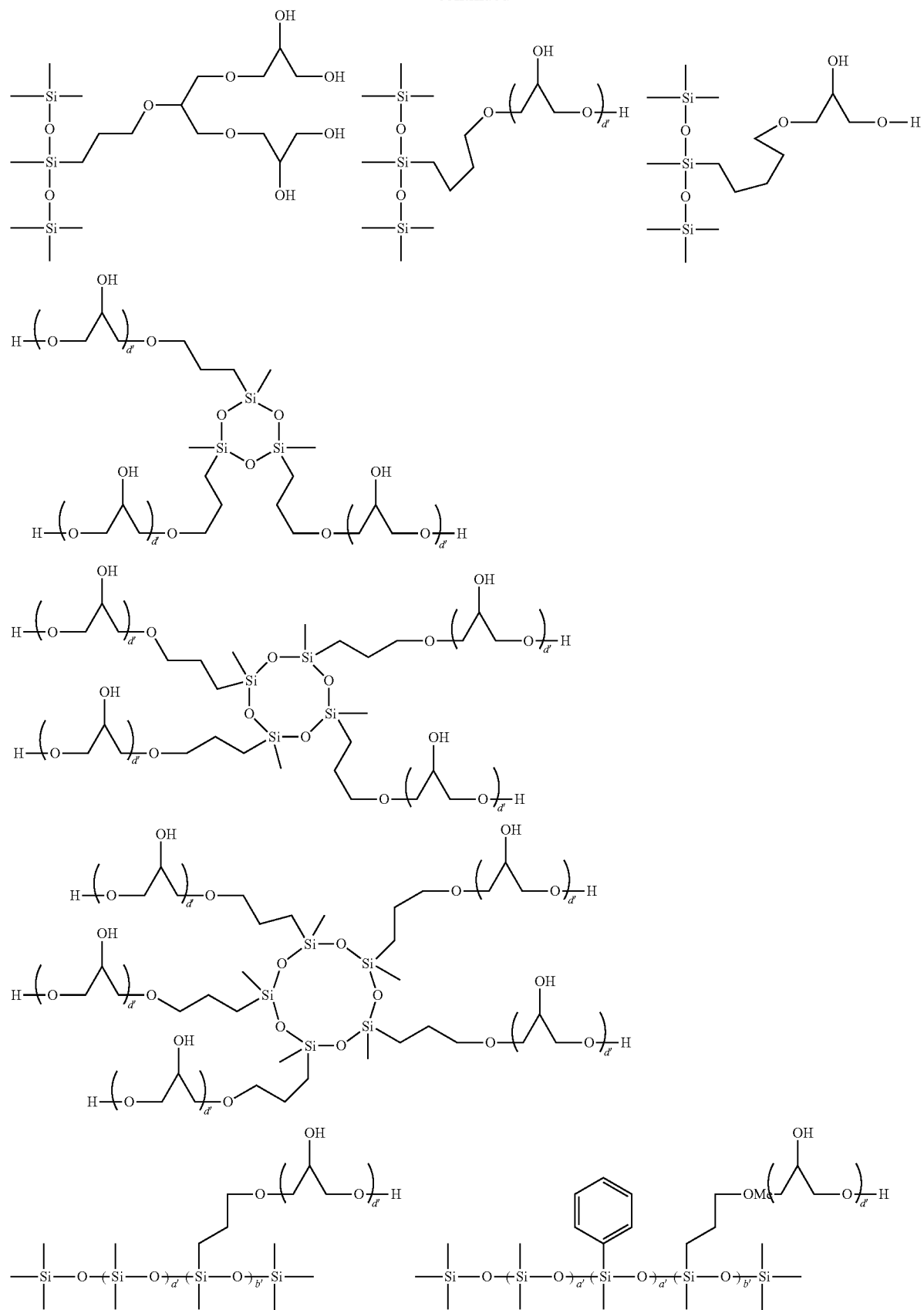

-continued
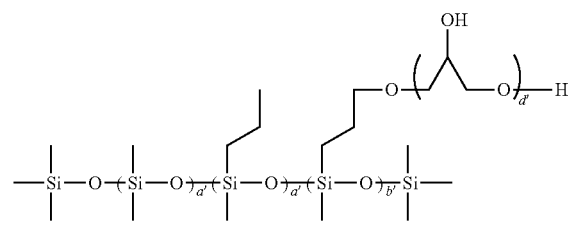
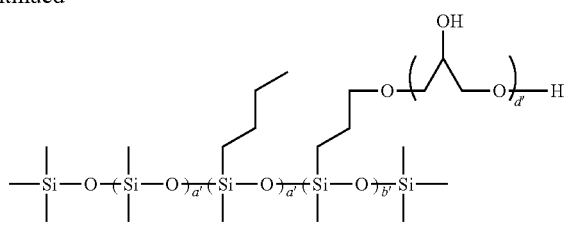
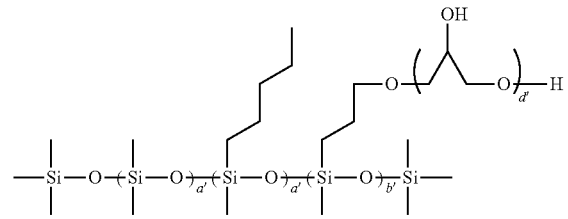
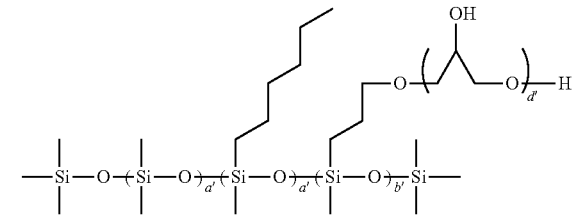
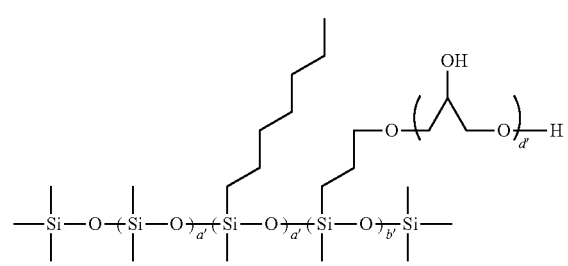
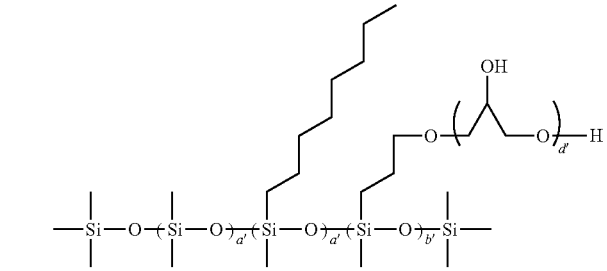
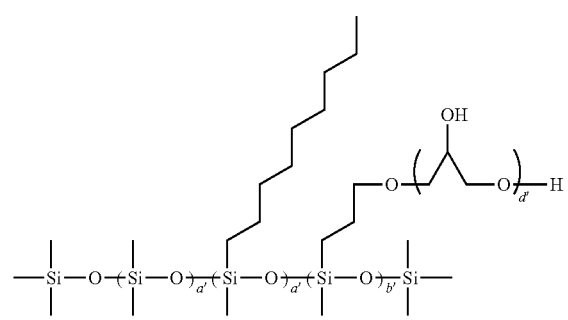
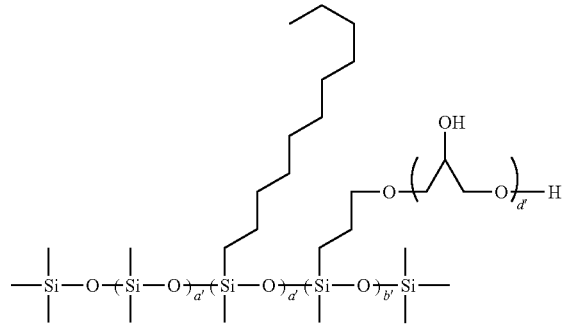
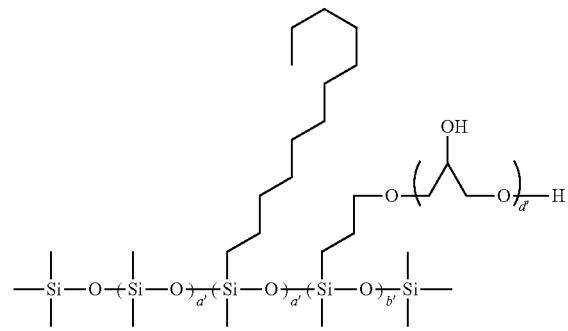
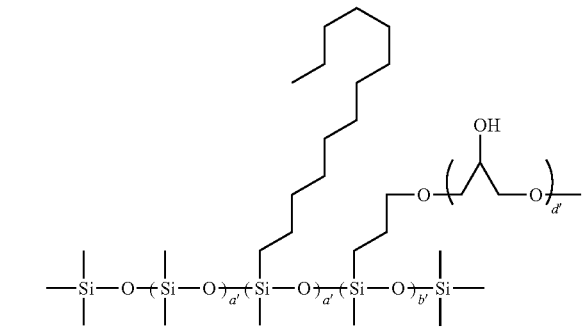
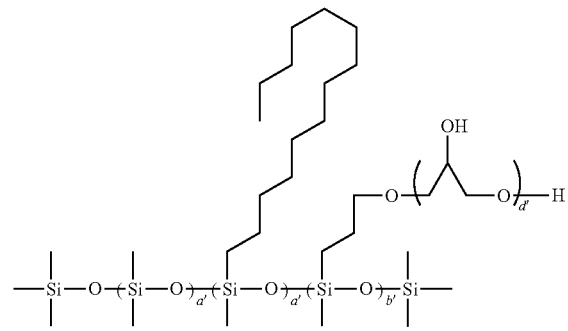
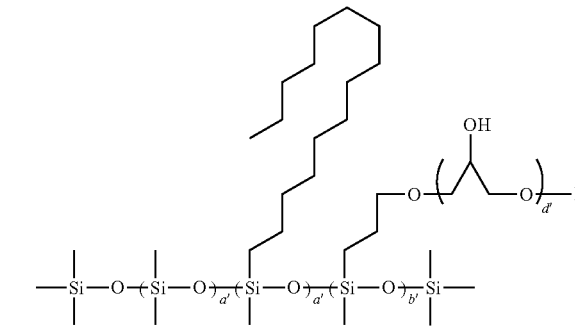

-continued
| 29 | 30 |
|---|---|
| 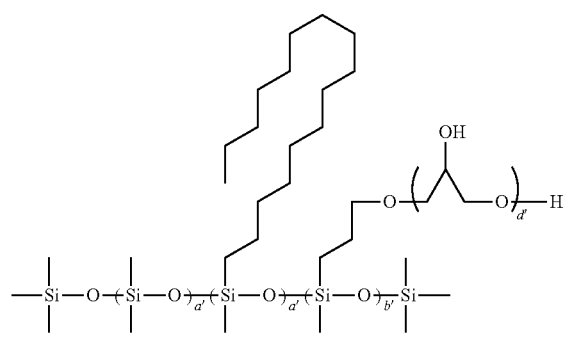 | 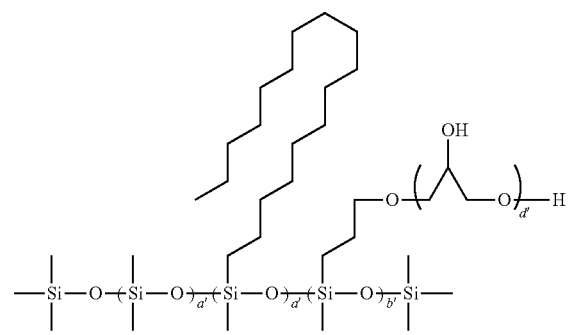 |
| 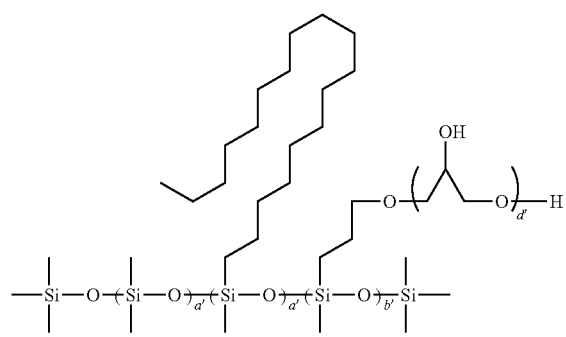 | 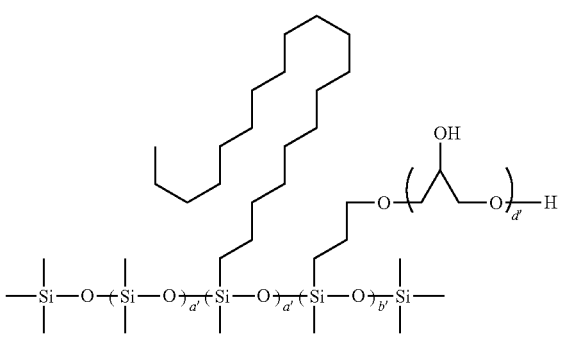 |
| 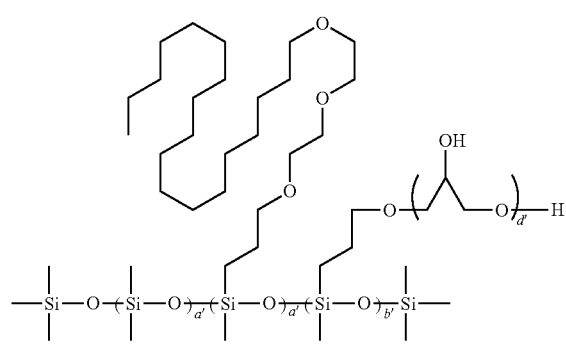 | 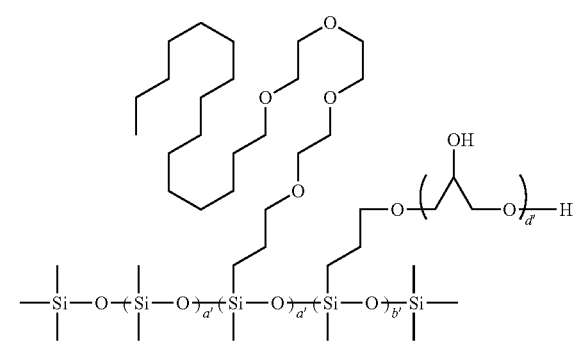 |
| 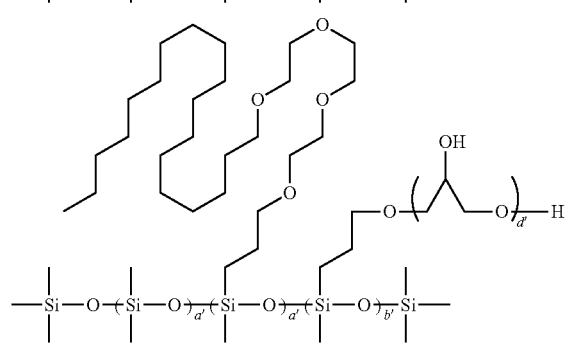 | 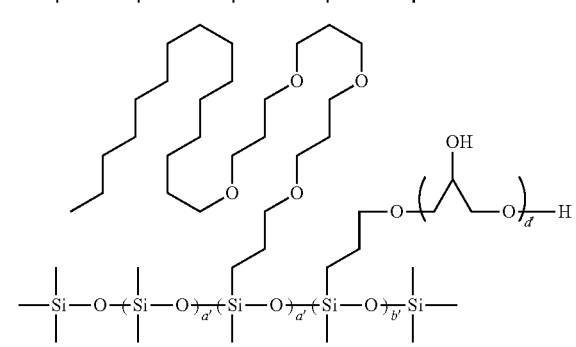 |
| 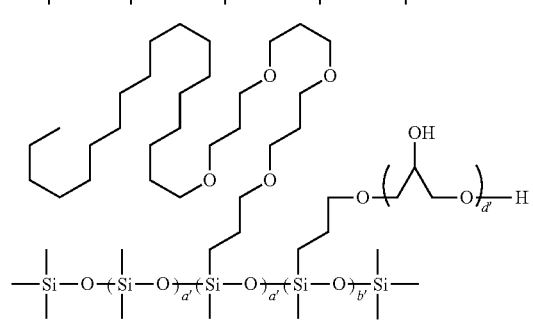 | 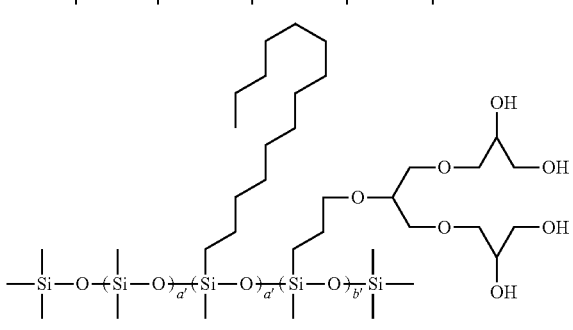 |

31 32
-continued
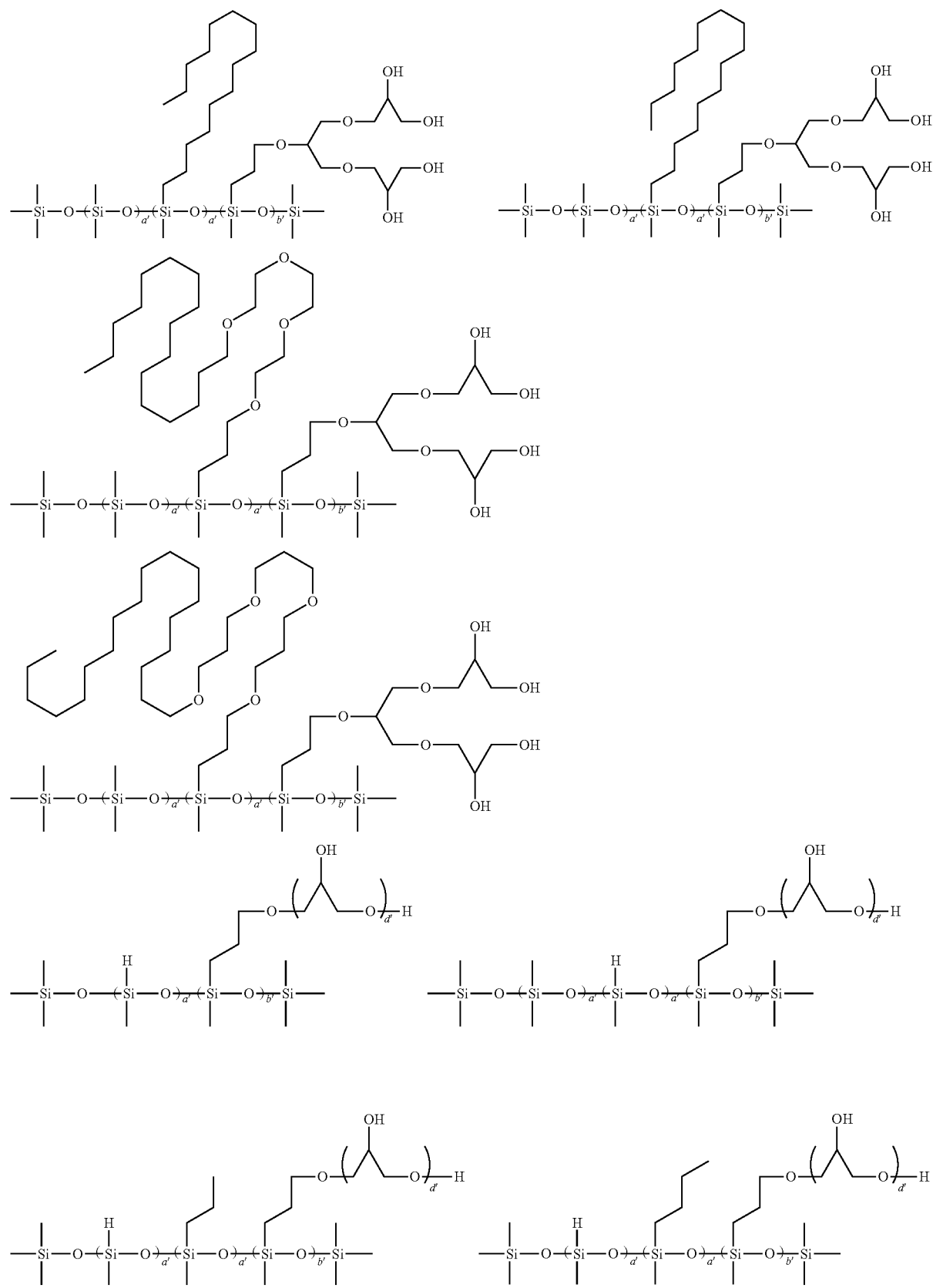

-continued
33
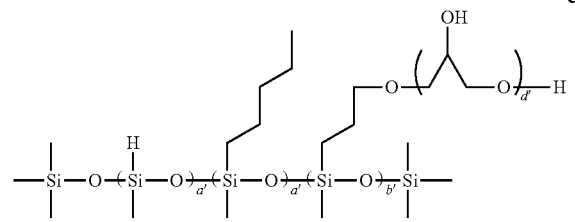
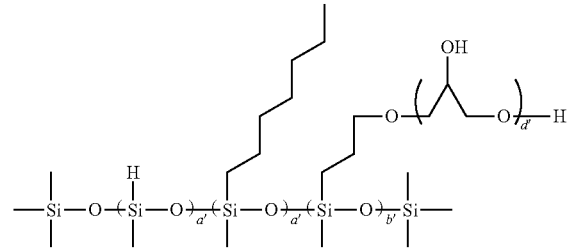
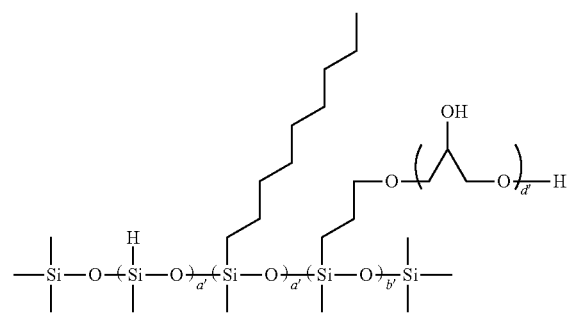
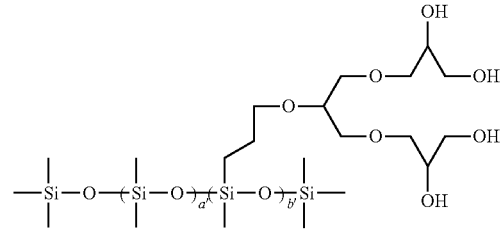
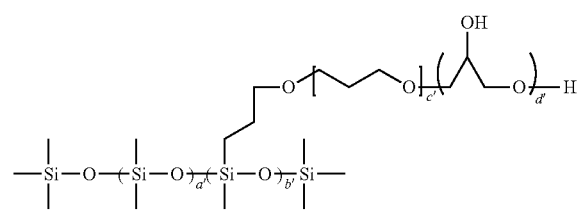
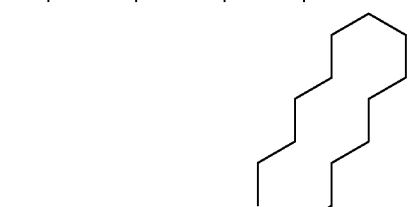
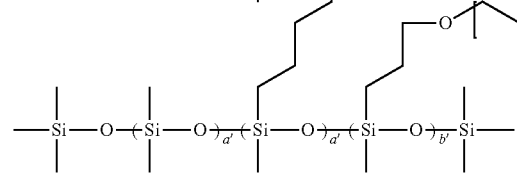
34
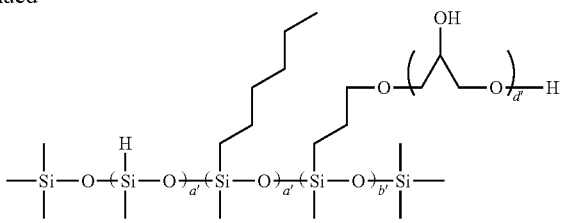
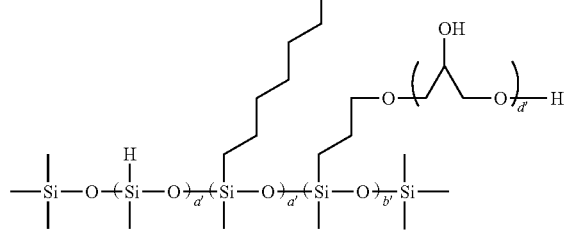
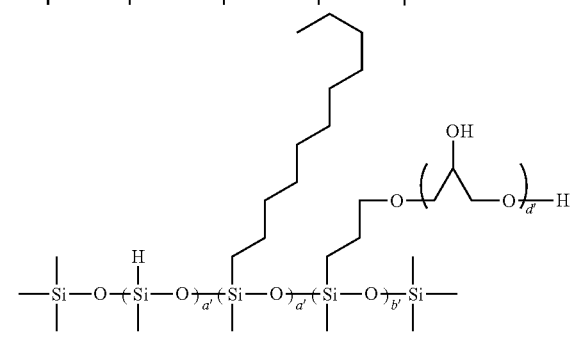
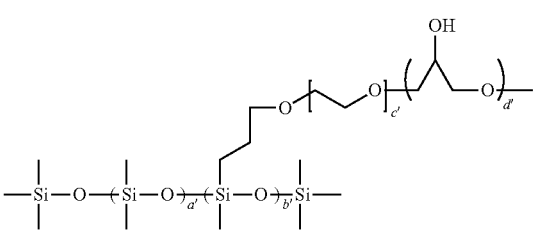
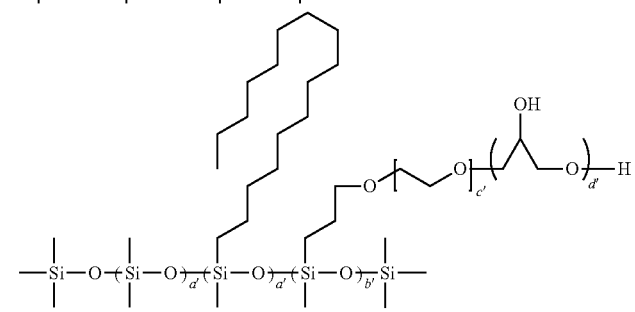
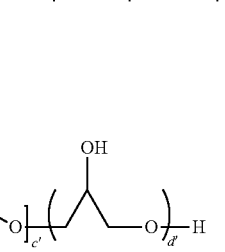

-continued
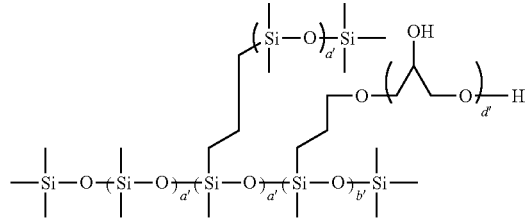
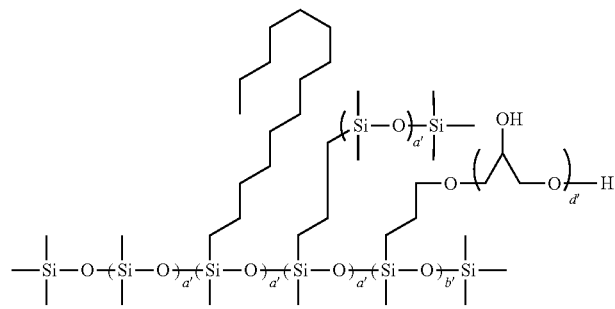
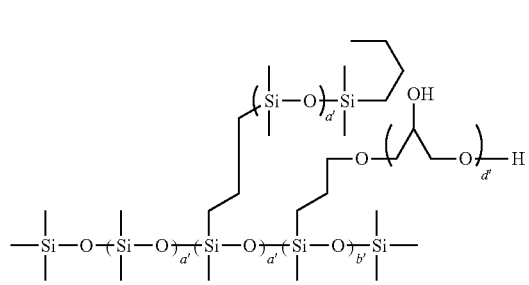
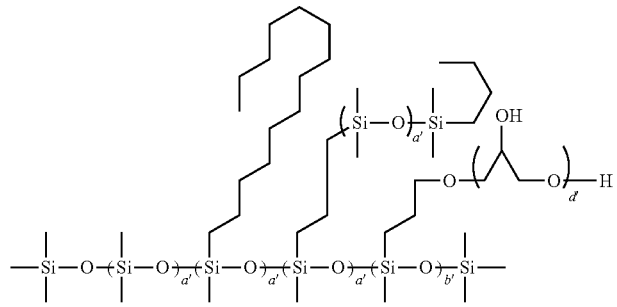
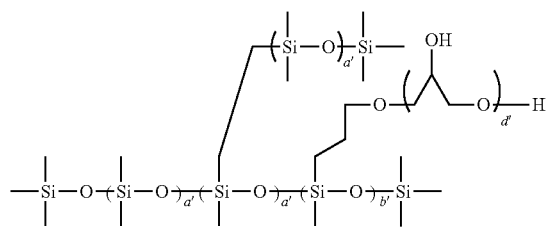
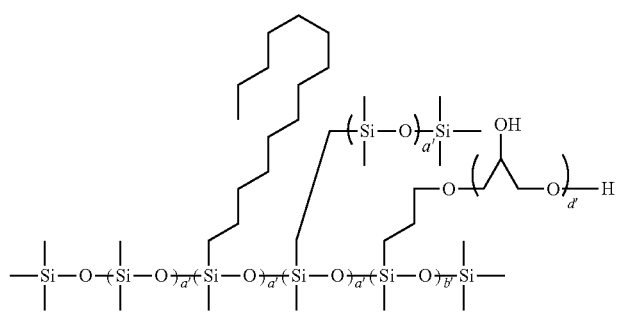
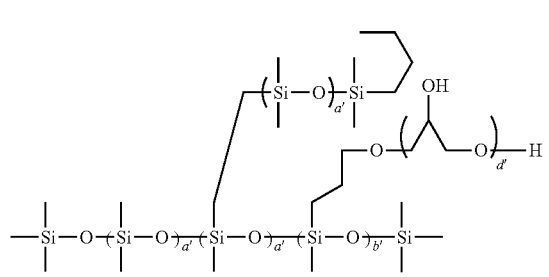
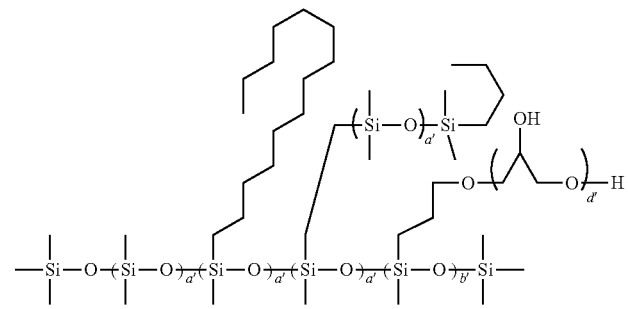
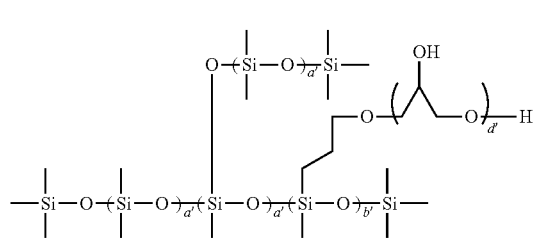
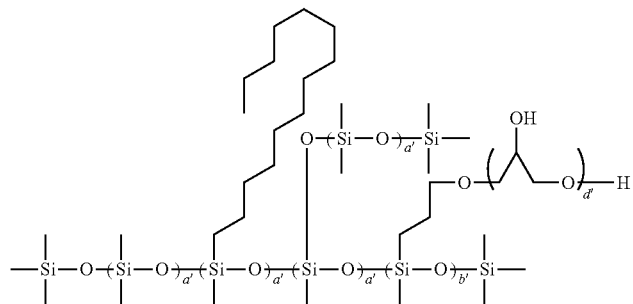

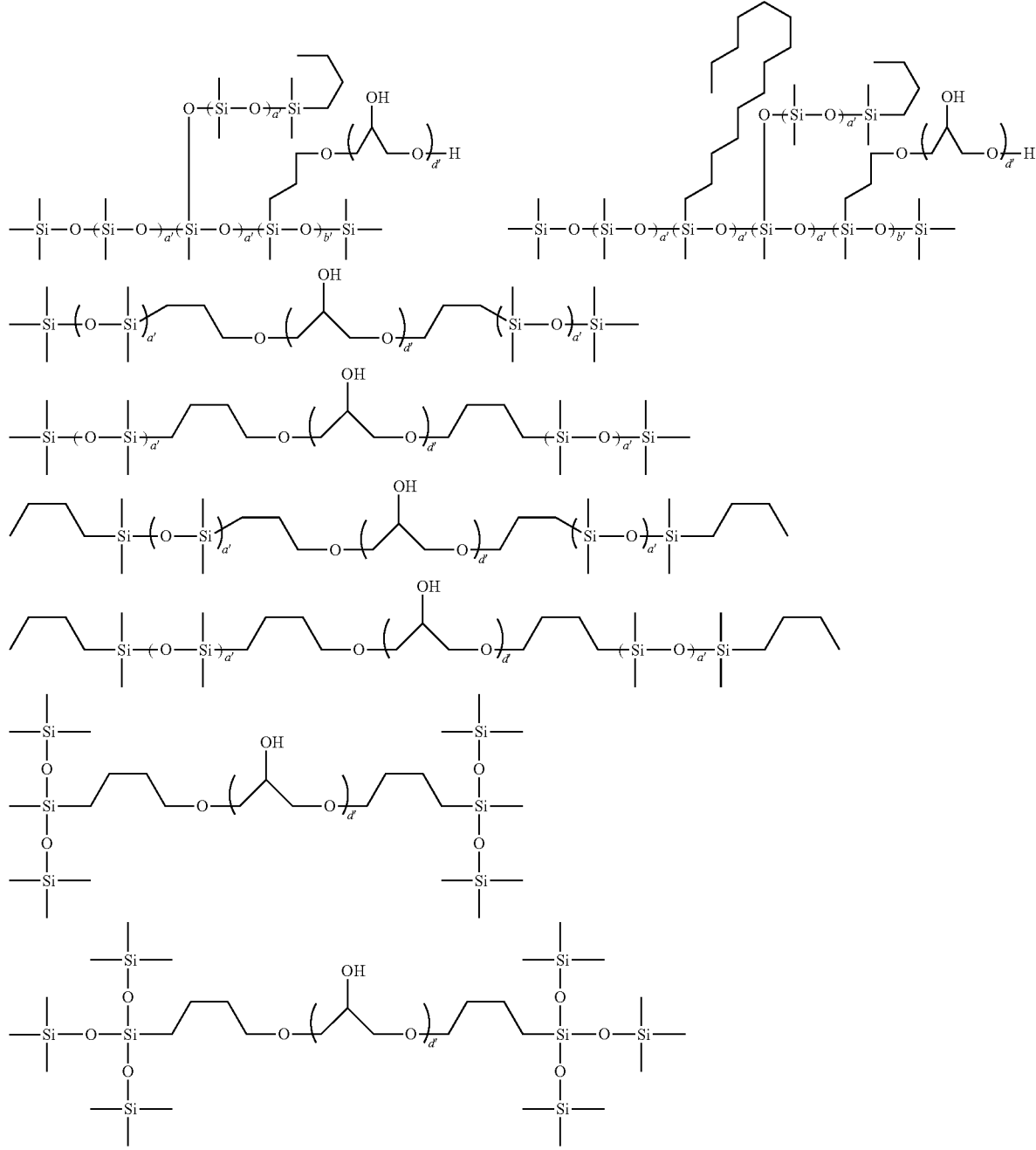

In the formulae, a', b', c' and d' are as defined above.

When such a silicone compound having a polyglycerin structure is incorporated, the resulting bio-electrode composition can form a living body contact layer that is capable of exhibiting more excellent moisture-holding property and consequently exhibiting more excellent sensitivity to ions released from skin.

(Other Additives)

The bio-electrode composition can be mixed with inorganic particles, such as silica particles, alumina particles, titania particles, and zirconia particles. Silica particles, alumina particles, titania particles, and zirconia particles have hydrophilic surfaces and favorable compatibility with hydrophilic ion polymer and polyglycerin silicone, and can improve the dispersibility of the ionic polymer and polyglycerin silicone in the hydrophobic silicone adhesive. The silica particles, alumina particles, titania particles, and zirconia particles may be either dry type or wet type both of which are preferably usable. The silica particles, alumina particles, titania particles, and zirconia particles may have any shape of spherical, elliptical, irregular, hollow, and porous shapes. Moreover, the surfaces of the silica particles and so forth may be modified with a silane coupling agent, silicone, etc.

<Method for Producing Bio-Electrode Composition>

The method for producing the inventive bio-electrode composition is not particularly limited. For example, the production method may include:

storing (A) an ionic polymer material, (B) an addition reaction-curable silicone having at least a hydrosilyl group, and (C) a platinum-group catalyst in separate containers; and mixing these components to produce a bio-electrode composition when a bio-electrode is manufactured.

Preferably, after the ionic polymer material and organohydrogensiloxane having a hydrosilyl group placed and stored in different containers as described above, these are blended with the platinum-group catalyst immediately before curing by the hydrosilylation reaction, and then the mixture is applied to form a film and baked for the curing by hydrosilylation reaction. This is because a solvent containing an ionic polymer compound contains a small amount of water even after the dehydration treatment for water removal, so that silanol is gradually formed during long-term storage.

In addition, when the component (D) is incorporated, the component (D) may mix into the component (A) or (B) before or at the same time when blending the component (C).

This can minimize the influence of water derived from the component (D).

(Dehydration Treatment)

As described above, water is likely to be incorporated into a solution containing the ionic polymer material of the component (A) including a polar solvent, but not the silicone having a hydrosilyl group of the component (B). When water contained in the solution (A) is mixed with the solution (B), the water causes the deactivation reaction of the hydrosilyl group. For this reason, the solution containing the ionic polymer compound of the component (A) is subjected to dehydration treatment as necessary. The dehydration treatment can be performed according to a conventional method, for example, through azeotropic dehydration to increase the concentration of the solution containing the ionic polymer compound or with a dehydrator, such as molecular sieves.

As has been described above, the inventive bio-electrode composition makes it possible to form a living body contact layer for a bio-electrode that is capable of efficiently conducting electric signals from skin to a device (i.e., excellent in electric conductivity), free from a risk of causing allergies even when the bio-electrode is attached to skin for a long period (i.e., excellent in biocompatibility), light-weight, manufacturable at low cost, and free from significant reduction in the electric conductivity even when the bio-electrode is wetted with water or dried. Moreover, it is possible to further enhance the electric conductivity by adding electro-conductive powder (such as carbon powder, metal powder), and it is possible to manufacture a bio-electrode with particularly high adhesive strength and high stretchability by combining the inventive bio-electrode composition with a resin having adhesion and stretchability. Further, the stretchability and adhesion to skin can be enhanced with an additive and so forth. The stretchability and adhesion can also be controlled by appropriately adjusting the composition of the resin and the thickness of the living body contact layer.

<Bio-Electrode>

The present invention also provides a bio-electrode including an electro-conductive base material and a living body contact layer formed on the electro-conductive base material, the living body contact layer being a cured product of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is formed from a cured product of the inventive bio-electrode composition. The living body contact layer 3 can contain a resin 6, an ionic polymer 5, and an electric conductivity improver 4. Hereinbelow, with reference to FIGS. 1 and 2, the living body contact layer 3 is described as a layer in which the electric conductivity improver 4 and the ionic polymer 5 are dispersed in the resin 6. Nevertheless, the inventive bio-electrode is not limited to this embodiment.

When the bio-electrode 1 as shown in FIG. 1 is used, the living body contact layer 3 (i.e., the layer in which the electric conductivity improver 4 and the ionic polymer 5 are dispersed in the resin 6) is brought into contact with a living body 7 as shown in FIG. 2. Electric signals are picked from the living body 7 through the electric conductivity improver 4 and the ionic polymer 5, and then conducted to a sensor device or the like (not shown) via the electro-conductive base material 2. As described above, the inventive bio-electrode is capable of coping with both electric conductivity and biocompatibility by using the ionic polymer and the electric conductivity improver described above, and obtaining electric signals from skin stably in high sensitivity because the contact area with the skin is kept constant due to the adhesion thereof.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device etc., and conducts electrical signals picked from a living body through the living body contact layer to the sensor device etc.

The electro-conductive base material is not particularly limited, as long as it has electric conductivity. The electro-conductive base material preferably contains one or more selected from the group consisting of gold, silver, silver chloride, platinum, aluminum, magnesium, tin, tungsten, iron, copper, nickel, stainless steel, chromium, titanium, carbon, and electro-conductive polymer, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode has a living body contact layer formed on the electro-conductive base material. This living body contact layer is a part to be actually in contact with a living body when the bio-electrode is used. The living body contact layer has electric conductivity and adhesion. The living body contact layer is a cured product of the inventive bio-electrode composition described above; that is, an adherent resin layer formed by mixing the components (A), (B), and (C), and applying the mixture, followed by curing. The components (A) and (B) may contain a polysiloxane having an alkenyl group, an MQ resin, and as necessary the component (D) and/or the component (E).

The living body contact layer preferably has an adhesive strength in a range of 0.5 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). Human skin is hard to adhere.

The living body contact layer of the bio-electrode has a thickness of preferably 1 μm or more and 5 mm or less, more preferably 2 μm or more and 3 mm or less. As the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be additionally provided with an adherent film on the living body contact layer as in conventional bio-electrodes (e.g., the bio-electrode described in JP 2004-033468A) in order to prevent peeling off of the bio-electrode from a living body during the use. When the adherent film is provided separately, the adherent film may be formed by using a raw material for the adherent film such as an acrylic type, a urethane type, and a silicone type. Particularly, the silicone type is suitable because of: the high oxygen permeability, which enables dermal respiration while the electrode is attached to the skin; the high water repellency, which suppresses lowering of adhesion due to perspiration; and the low irritation to skin. It is to be noted that the inventive bio-electrode does not necessarily require this adherent film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ ones described in JP 2004-033468A.

As described above, since the inventive bio-electrode includes the living body contact layer formed from the cured product of the aforementioned inventive bio-electrode composition, the inventive bio-electrode is capable of efficiently conducting electric signals from skin to a device (i.e., excellent in electric conductivity), does not cause allergies even after long-period attachment to skin (i.e., excellent in biocompatibility), is light-weight and manufacturable at low cost, and prevents significant reduction in the electric conductivity even when wetted with water or dried. In addition, it is possible to further improve the electric conductivity by adding an electro-conductive powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode as described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

Note that the electro-conductive base material etc. used in the inventive method for manufacturing a bio-electrode may be the same as those described above.

The method for applying the bio-electrode composition onto the electro-conductive base material is not particularly limited. Examples of the suitable method include dip coating, spray coating, spin coating, roll coating, flow coating, doctor coating, screen printing, flexographic printing, gravure printing, inkjet printing, etc.

The method for curing the resin is not particularly limited and can be appropriately selected based on the kind of the components (A) and (B) used for the bio-electrode composition. For example, either or both of heat and light activate the platinum-group catalyst, and the bio-electrode composition is preferably cured by addition reaction of the hydrosilyl group and alkenyl group bonded to the silicone in the composition.

The heating temperature is not particularly limited and may be appropriately selected based on the kind of the components (A) and (B) used for the bio-electrode composition, but is preferably about 50 to 250° C., for example.

When combining the heating and light irradiation, it is possible to perform the heating and the light irradiation simultaneously, to perform the light irradiation and then the heating, or to perform the heating and then the light irradiation. It is also possible to perform air-drying to evaporate the solvent before heating the applied film.

If the components (A) and (B) have high water contents, or if the component (A) is a mixture with a solvent containing a hydroxy group, a carboxyl group, a nitrogen atom, or a thiol group, the deactivation reaction of the hydrosilyl group starts immediately after mixing the components (A) and (B). In these cases, the mixture of the components (A), (B), and (C) is allowed to stand, the printed and cured bio-electrode is attached to skin in order to collect biological signals to be peeled, and then a residue is left on the skin. This is caused by a cohesive failure which results from lowering the crosslinking density in the bio-electrode film due to the deactivation of the hydrosilyl group. Similar phenomena will also occur even when the printing is quickly performed after the mixing of the components, if the time until curing by baking and so forth is long.

Water droplets may be attached to the surface of the cured film; alternatively, the film surface may be sprayed with water vapor or mist. These treatments improve the compatibility with skin, and enable quick collection of biological signals. Water mixed with alcohol can be used to reduce size of water vapor or mist. The film surface may be wetted by bringing an absorbent cotton or cloth containing water into contact therewith.

The water for making the surface of the cured film wet may contain a salt. The water-soluble salt mixed with the water may be selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the polymer compound (A) described above is excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl isethionate, sodium lauroyl methylalanine, sodium methyl cocoyl taurate, sodium cocoyl glutamate, sodium cocoyl sarcosinate, sodium lauroyl methyl taurate, lauramidopropyl, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water-soluble salt can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formula (4) or (5).

In the pretreatment methods with the aqueous solution containing the water-soluble salt, the cured bio-electrode film can be wetted by a spraying method, a droplet-dispensing method, etc. The bio-electrode film can also be wetted under a high-temperature, high-humidity condition like sauna. To prevent drying after the wetting, a protective film can be further stacked on the permeated layer to cover the surface. Since the protective film needs to be removed immediately before the bio-electrode is attached to skin, the protective film may be coated with a release agent, or a peelable Teflon (registered trademark) film may be used as the protective film. For long-time storage, the dry electrode covered with the peelable film is preferably sealed in a bag that is covered with aluminum etc. To prevent drying in the bag covered with aluminum, it is preferable to include water therein, too.

Before the inventive bio-electrode is attached to skin, the skin may be moisturized with water, alcohol, etc., or the skin may be wiped with a cloth or absorbent cotton containing water, alcohol, etc. The water and the alcohol may contain the above-described salts.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

EXAMPLE

Hereinafter, the present invention will be specifically described with reference to Examples and Comparative Examples, but the present invention is not limited thereto. Incidentally, "Me" represents a methyl group, and "Vi" represents a vinyl group.

Synthesis Example 1

A solution of Ionic polymer 1, which was blended as an ionic material (conductive material) to a bio-electrode composition, was synthesized as follows. First, 20 mass % solutions of corresponding monomers in PGMEA were introduced into a reaction vessel and mixed. The reaction vessel was cooled to −70° C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.01 moles per 1 mole of the whole monomers. This was warmed to 60° C. and then allowed to react for 15 hours. The PGMEA was evaporated with an evaporator to concentrate the polymer to 30 mass % and to evaporate water simultaneously. After a portion of the polymer solution was dried, the composition of the resulting polymer was identified by $^1$H-NMR. The molecular weight (Mw) and the dispersity (Mw/Mn) of the obtained polymer were determined by gel permeation chromatography (GPC) using tetrahydrofuran (THF) as a solvent.

30 mass % solution of Ionic polymer 1 in PGMEA
Mw=38,100
Mw/Mn=1.91

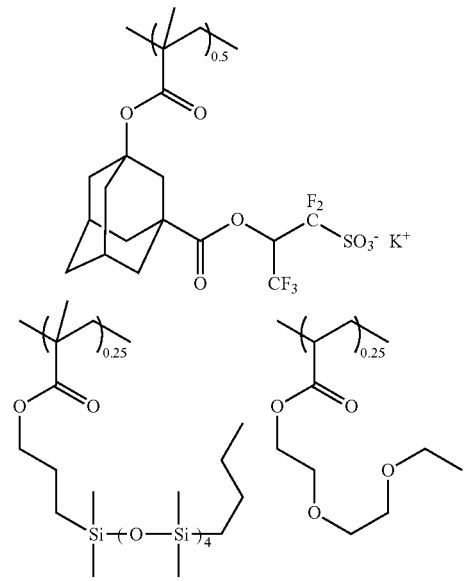

The repeating number in each formula shows the average value.

Synthesis Example 2

A solution of Ionic polymer 2 was prepared by the same method as in Synthesis Example 1, but 2-heptanone was used as the polymerization solvent.

30 mass % solution of Ionic polymer 2 in 2-heptanone
Mw=32,100
Mw/Mn=1.99

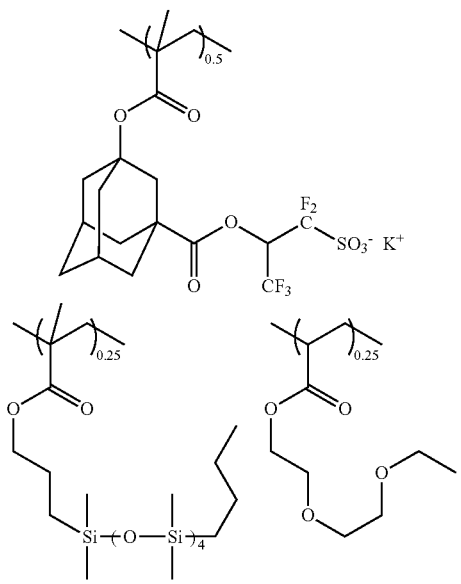

The repeating number in each formula shows the average value.

Synthesis Example 3

A solution of Ionic polymer 3 was prepared by the same method as in Synthesis Example 1, but 2-ethoxy carbonyl cyclopentanone was used as the polymerization solvent.

30 mass % solution of Ionic polymer 3 in 2-ethoxy carbonyl cyclopentanone
Mw=33,300
Mw/Mn=1.83

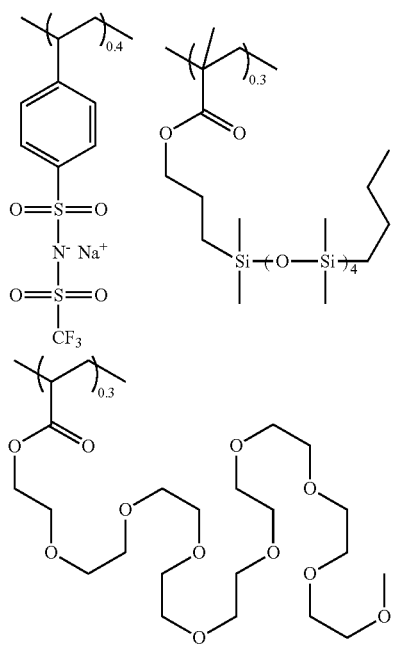

The repeating number in each formula shows the average value.

Synthesis Example 4

A solution of Ionic polymer 4 was prepared by the same method as in Synthesis Example 1, but cyclohexanone was used as the polymerization solvent.

30 mass % solution of Ionic polymer 4 in cyclohexanone
Mw=80,100
Mw/Mn=2.15

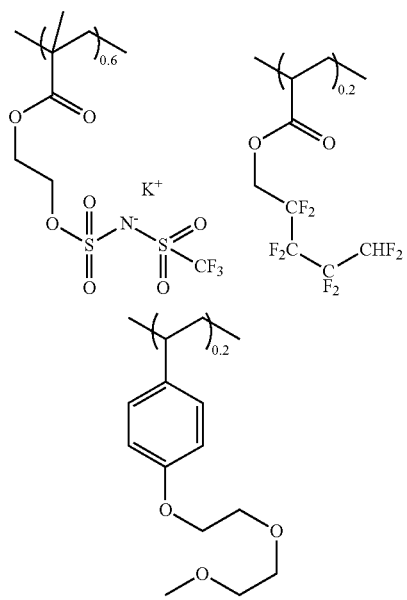

Synthesis Example 5

A solution of Ionic polymer 5 was prepared by the same method as in Synthesis Example 1, but cyclopentanone was used as the polymerization solvent.

30 mass % solution of Ionic polymer 5 in cyclopentanone
Mw=44,400
Mw/Mn=1.94

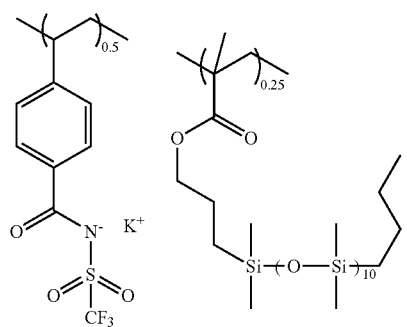

-continued

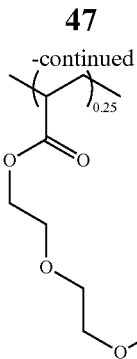

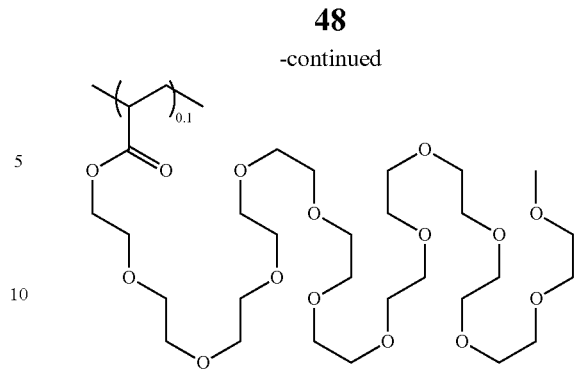

The repeating number in each formula shows the average value.

Synthesis Example 6

A solution of Ionic polymer 6 was prepared by the same method as in Synthesis Example 1, but 2-propylcyclohexanone was used as the polymerization solvent.

30 mass % solution of Ionic polymer 6 in 2-propylcyclohexanone
Mw=41,100
Mw/Mn=1.86

Synthesis Example 8

A solution of Ionic polymer 8 was prepared by the same method as in Synthesis Example 1, but 2-pentyl-2-cyclopenten-1-one was used as the polymerization solvent.

30 mass % solution of Ionic polymer 8 in 2-pentyl-2-cyclopenten-1-one
Mw=35,700
Mw/Mn=2.06

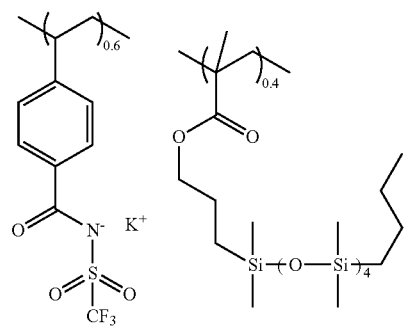

The repeating number in each formula shows the average value.

Synthesis Example 7

A solution of Ionic polymer 7 was prepared by the same method as in Synthesis Example 1, but 2-acetylcyclohexanone was used as the polymerization solvent.

30 mass % solution of Ionic polymer 7 in 2-acetylcyclohexanone
Mw=43,600
Mw/Mn=1.93

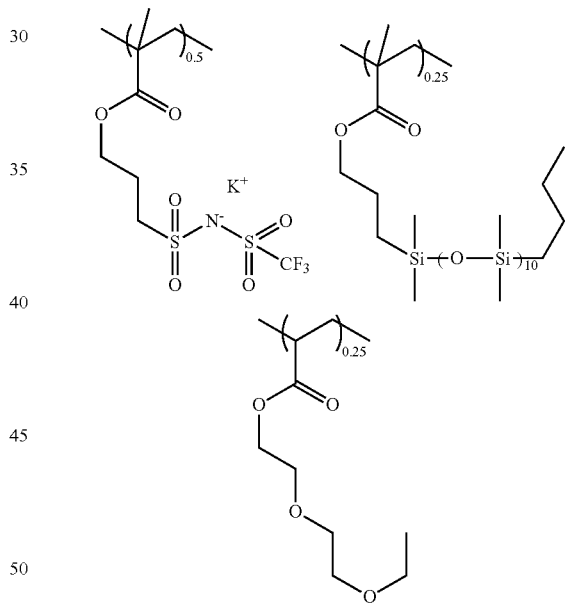

The repeating number in each formula shows the average value.

Synthesis Example 9

A solution of Ionic polymer 9 was prepared by the same method as in Synthesis Example 1, but 2-heptylcyclopentanone was used as the polymerization solvent.

30 mass % solution of Ionic polymer 9 in 2-heptylcyclopentanone
Mw=55,100
Mw/Mn=2.02

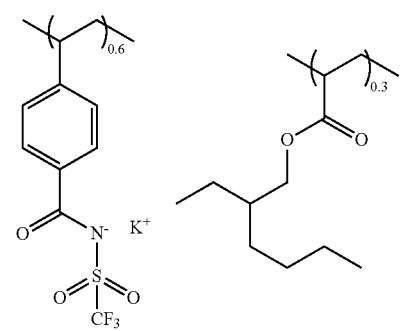

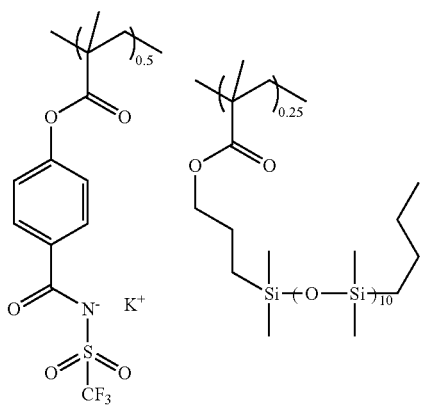

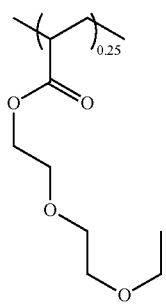

The repeating number in each formula shows the average value.

Synthesis Example 10

A solution of Ionic polymer 10 was prepared by the same method as in Synthesis Example 1, but 3,3,5-trimethylcyclohexanone was used as the polymerization solvent.

30 mass % solution of Ionic polymer 10 in 3,3,5-trimethylcyclohexanone

Mw=87,500

Mw/Mn=2.01

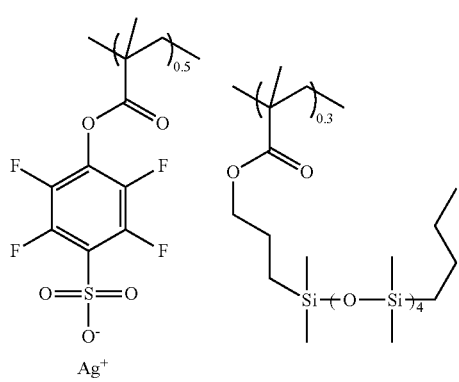

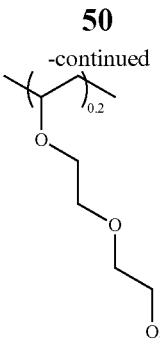

The repeating number in each formula shows the average value.

Synthesis Example 11

A solution of Ionic polymer 11 was prepared by the same method as in Synthesis Example 1, but 2-methoxy carbonyl cyclopentanone was used as the polymerization solvent.

30 mass % solution of Ionic polymer 11 in 2-methoxy carbonyl cyclopentanone

Mw=41,600

Mw/Mn=1.91

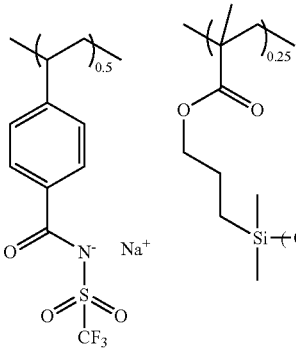

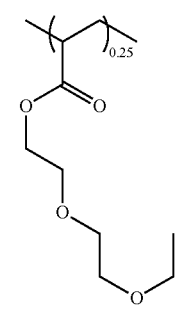

The repeating number in each formula shows the average value.

Synthesis Example 12

A solution of Ionic polymer 12 was prepared by the same method as in Synthesis Example 1, but γ-valerolactone was used as the polymerization solvent.

30 mass % solution of Ionic polymer 12 in γ-valerolactone

Mw=36,100

Mw/Mn=1.55

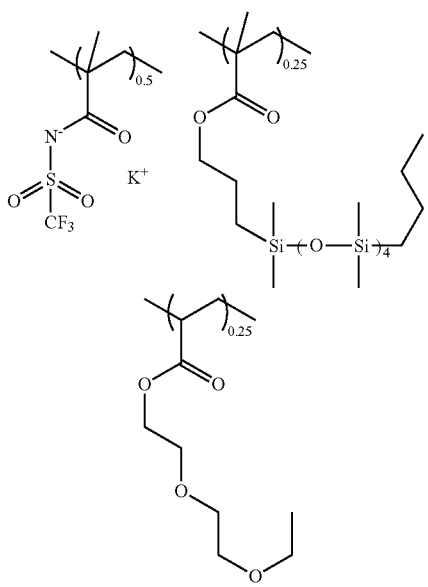

The repeating number in each formula shows the average value.

Synthesis Example 13

A solution of Ionic polymer 13 was prepared by the same method as in Synthesis Example 1, but ε-caprolactone was used as the polymerization solvent.

30 mass % solution of Ionic polymer 13 in ε-caprolactone
Mw=38,300
Mw/Mn=2.01

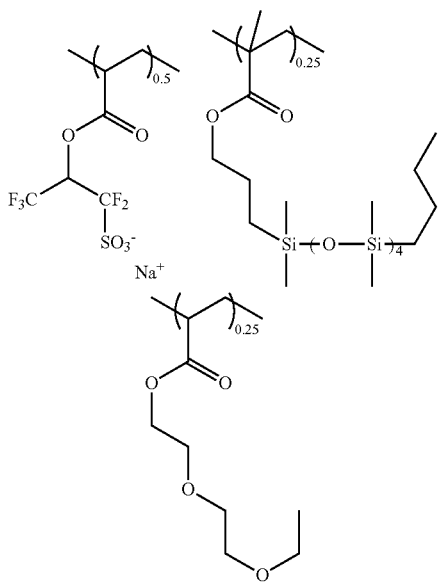

The repeating number in each formula shows the average value.

Synthesis Example 14

A solution of Ionic polymer 14 was prepared by the same method as in Synthesis Example 1, but cycloheptanone was used as the polymerization solvent.

30 mass % solution of Ionic polymer 14 in cycloheptanone
Mw=33,500
Mw/Mn=1.97

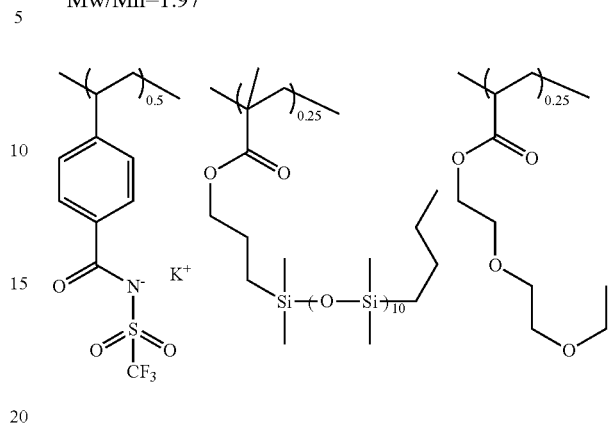

The repeating number in each formula shows the average value.

Synthesis Example 15

A solution of Ionic polymer 15 was prepared by the same method as in Synthesis Example 1, but 3-methylcyclohexanone was used as the polymerization solvent.

30 mass % solution of Ionic polymer 15 in 3-methylcyclohexanone
Mw=34,900
Mw/Mn=1.91

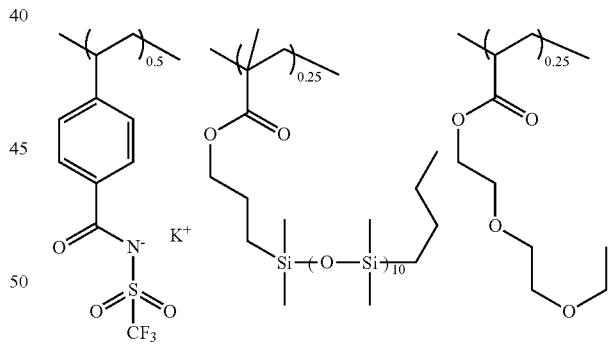

The repeating number in each formula shows the average value.

Synthesis Example 16

A solution of Ionic polymer 16 was prepared by the same method as in Synthesis Example 1, but diethylene glycol diethyl ether was used as the polymerization solvent.

30 mass % solution of Ionic polymer 16 in diethylene glycol diethyl ether
Mw=43,100
Mw/Mn=1.74

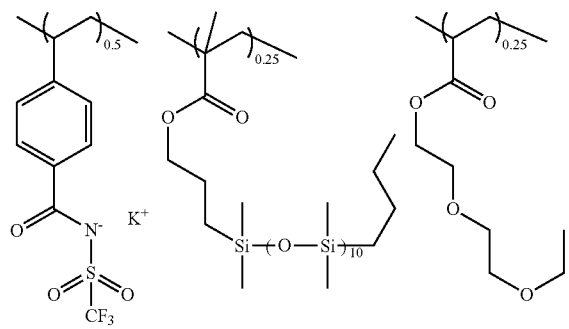

The repeating number in each formula shows the average value.

Synthesis Example 17

A solution of Ionic polymer 17 was prepared by the same method as in Synthesis Example 1, but diethylene glycol methyl butyl ether was used as the polymerization solvent.
30 mass % solution of Ionic polymer 17 in diethylene glycol methyl butyl ether
Mw=42,000
Mw/Mn=1.77

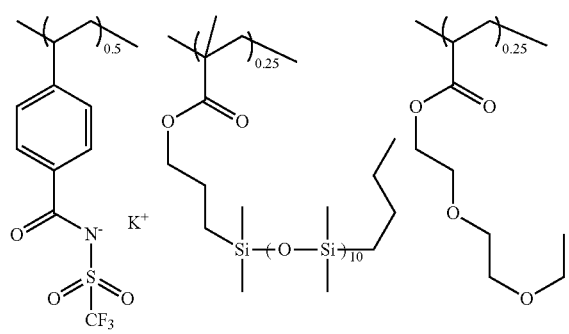

The repeating number in each formula shows the average value.

Synthesis Example 18

A solution of Ionic polymer 18 was prepared by the same method as in Synthesis Example 1, but diethylene glycol dibutyl ether was used as the polymerization solvent.
30 mass % solution of Ionic polymer 18 in diethylene glycol dibutyl ether
Mw=41,000
Mw/Mn=1.69

The repeating number in each formula shows the average value.

Synthesis Example 19

A solution of Ionic polymer 19 was prepared by the same method as in Synthesis Example 1, but diethylene glycol butyl ether acetate was used as the polymerization solvent.
30 mass % solution of Ionic polymer 19 in diethylene glycol butyl ether acetate
Mw=37,000
Mw/Mn=1.61

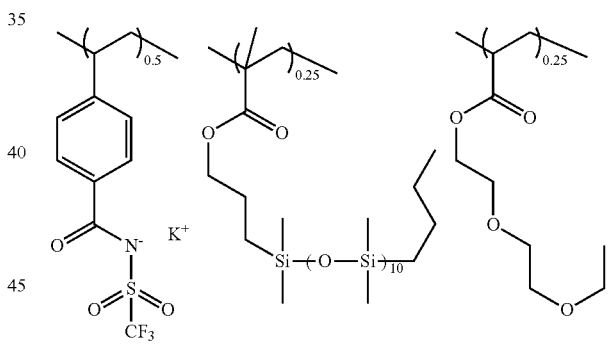

The repeating number in each formula shows the average value.

Synthesis Example 20

A solution of Ionic polymer 20 was prepared by the same method as in Synthesis Example 19, but the ion monomer was changed and diethylene glycol butyl ether acetate was used as the polymerization solvent.
30 mass % solution of Ionic polymer 20 in diethylene glycol butyl ether acetate
Mw=39,000
Mw/Mn=1.64

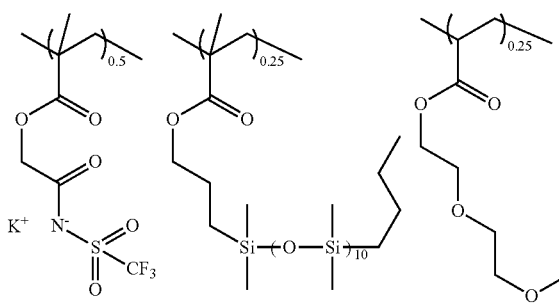

The repeating number in each formula shows the average value.

Synthesis Example 21

A solution of Ionic polymer 21 was prepared by the same method as in Synthesis Example 19, but the ion monomer was changed and diethylene glycol butyl ether acetate was used as the polymerization solvent.

30 mass % solution of Ionic polymer 21 in diethylene glycol butyl ether acetate

Mw=44,000

Mw/Mn=1.68

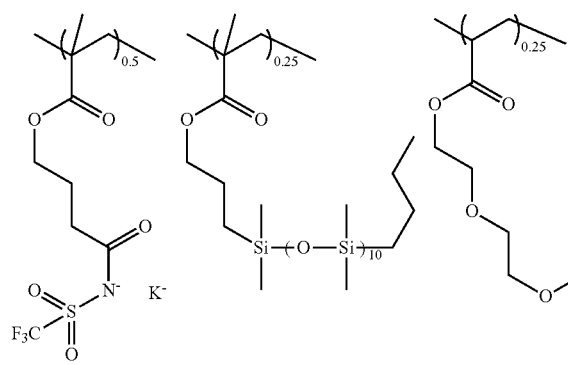

The repeating number in each formula shows the average value.

Synthesis Example 22

A solution of Ionic polymer 22 was prepared by the same method as in Synthesis Example 19, but the ion monomer was changed and diethylene glycol butyl ether acetate was used as the polymerization solvent.

30 mass % solution of Ionic polymer 22 in diethylene glycol butyl ether acetate

Mw=48,000

Mw/Mn=1.81

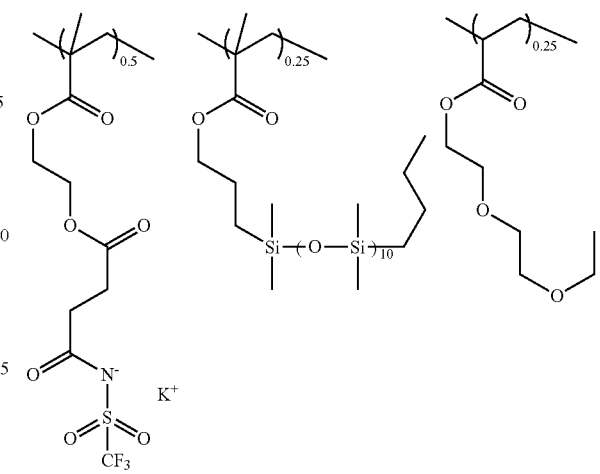

The repeating number in each formula shows the average value.

Comparative Synthesis Example 1

A solution of Comparative ionic polymer 1 was prepared by the same method as in Synthesis Example 1, but the polymerization was carried out using cyclopentanone as the polymerization solvent to make the polymer concentration of 30 mass %, and no dehydration treatment was performed.

30 mass % solution of Comparative ionic polymer 1 in cyclopentanone

Mw=44,400

Mw/Mn=1.98

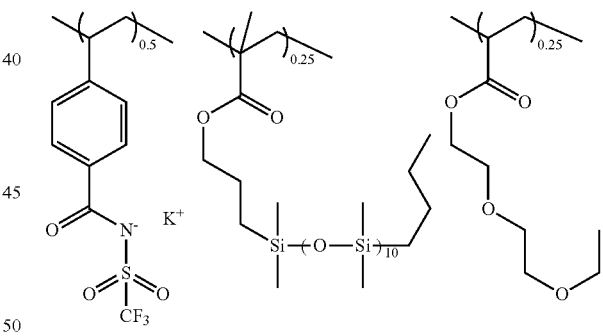

The repeating number in each formula shows the average value.

Comparative Synthesis Example 2

A solution of Comparative ionic polymer 2 was prepared by the same method as in Synthesis Example 1, but the polymerization was carried out using PGEE as the polymerization solvent to make the polymer concentration of 30 mass %, and no dehydration treatment was performed.

30 mass % solution of Comparative ionic polymer 2 in PGEE

Mw=46,600

Mw/Mn=1.95

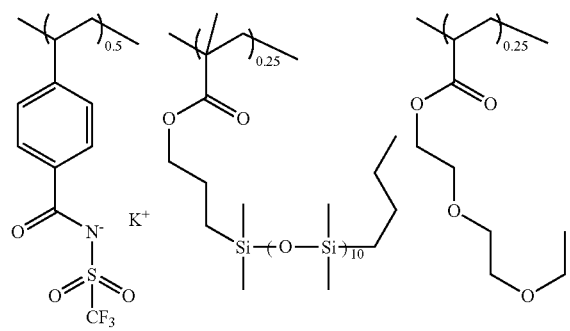
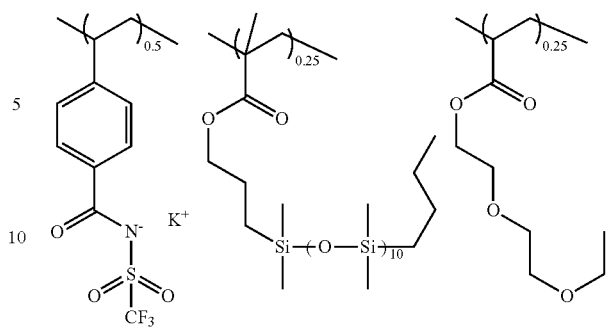

The repeating number in each formula shows the average value.

Comparative Synthesis Example 3

A solution of Comparative ionic polymer 3 was prepared by the same method as in Synthesis Example 1, but the polymerization was carried out using diacetone alcohol as the polymerization solvent.

30 mass % solution of Comparative ionic polymer 3 in diacetone alcohol
Mw=36,600
Mw/Mn=1.92

The repeating number in each formula shows the average value.

Polyglycerin-silicone compounds 1 to 5 (additive) are shown below. The synthesis method for these compounds is as disclosed in JP 2019-99469A. The compounds were synthesized through hydrosilylation reaction using a silicone compound having a SiH group and a polyglycerin compound having a double bond in the presence of a platinum catalyst.

Polyglycerin-silicone compound 1

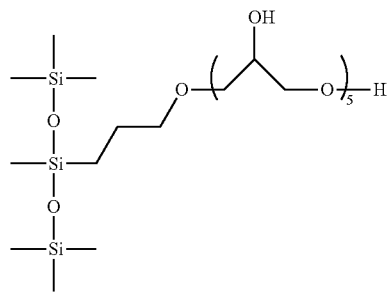

Polyglycerin-silicone compound 2

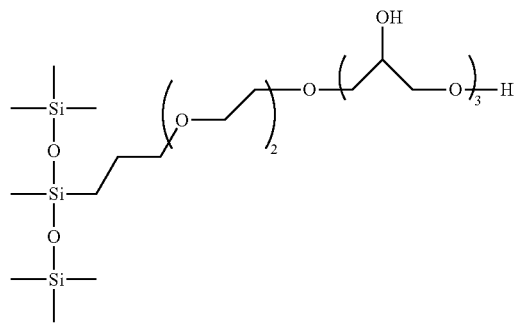

Polyglycerin-silicone compound 3

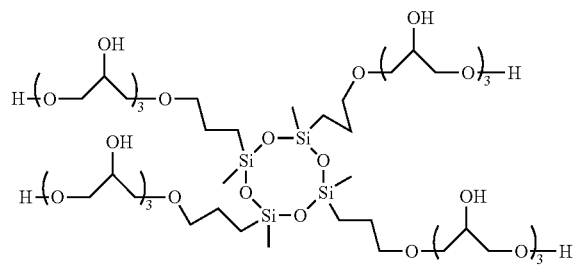

Polyglycerin-silicone compound 4

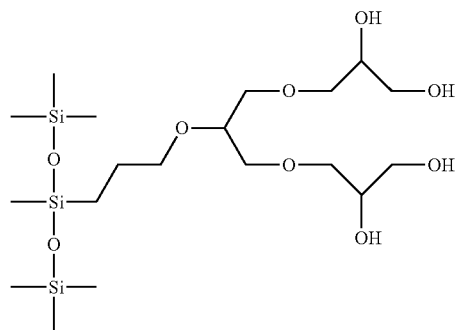

-continued

Polyglycerin-silicone compound 5

[Chemical structure diagram of Polyglycerin-silicone compound 5]

Siloxane compounds 1 to 4, which were blended as silicone-based resin to the bio-electrode compositions, are shown below.

(Siloxane Compound 1)

Siloxane compound 1 was vinyl group-containing polydimethylsiloxane having an alkenyl group-content of 0.007 mol/100 g in which the terminals of molecular chain were capped with $SiMe_2Vi$ groups, with the 30% solution in toluene having a viscosity of 27,000 mPa·s.

(Siloxane Compound 2)

Siloxane compound 2 was a 60% solution of polysiloxane of MQ resin composed of an $Me_3SiO_{0.5}$ unit and an $SiO_2$ unit ($Me_3SiO_{0.5}$ unit/$SiO_2$ unit=0.8) in ISOPAR G.

(Siloxane Compound 3)

Siloxane compound 3 was polydimethylsiloxane-bonded MQ resin obtained by heating a solution with refluxing for 4 hours, followed by cooling. The solution is composed of 40 parts by mass of vinyl group-containing polydimethylsiloxane having an alkenyl group-content of 0.007 mol/100 g in which the terminals of molecular chain were capped with OH groups, with the 30% solution in toluene having a viscosity of 42,000 mPa·s; 100 parts by mass of 60% solution of polysiloxane of MQ resin composed of an $Me_3SiO_{0.5}$ unit and an $SiO_2$ unit ($Me_3SiO_{0.5}$ unit/$SiO_2$ unit=0.8) in ISOPAR G; and 26.7 parts by mass of ISOPAR G.

(Siloxane Compound 4)

As a silicone having a hydrosilyl group, KF-99 manufactured by Shin-Etsu Chemical Co., Ltd. was used.

Moreover, as a silicone-based resin, KF-353 manufactured by Shin-Etsu Chemical Co., Ltd. was used, which is polyether type silicone oil with the side chain being modified with polyether.

Organic solvents blended to the bio-electrode compositions are shown below.
- PGMEA: propylene glycol-1-monomethyl ether-2-acetate
- PGEE: 1-ethoxy-2-propanol
- DAA: diacetone alcohol
- ISOPAR G: isoparaffin base solvent manufactured by Standard Sekiyu CO., LTD.
- ISOPAR M: isoparaffin base solvent manufactured by Standard Sekiyu CO., LTD.

Platinum catalyst, electric conductivity improvers (metal powder, carbon black, carbon nanotube, lithium titanate, graphite, ion-treated graphite, ion-treated carbon blacks, and metal chlorides), and additive (addition-reaction inhibitor), which were blended as additives to the bio-electrode compositions, are shown below.

Platinum catalyst: CAT-PL-56 (platinum content: 2 mass %) manufactured by Shin-Etsu Chemical Co., Ltd.

Metal Powders:
  silver powder: silver flake with the diameter of 10 μm manufactured by Sigma-Aldrich Co., LLC.
  gold powder: gold powder with the diameter of 10 μm or less manufactured by Sigma-Aldrich Co., LLC. Carbon black: DENKA BLACK Li-400 manufactured by Denka Co., Ltd.

Multilayer carbon nanotube: with the diameter of 110 to 170 nm and length of 5 to 9 μm manufactured by Sigma-Aldrich Co., LLC.

Lithium titanate powder, spinel: with the size of 200 nm or less manufactured by Sigma-Aldrich Co., LLC.

Graphite: with the diameter of 20 μm or less manufactured by Sigma-Aldrich Co., LLC.

Ion-treated graphite 1: prepared according to Preparation Example 1 below.

Ion-treated carbon blacks 1, 2: prepared according to Preparation Examples 2, 3 below.

Metal Chloride Powders:
  sodium chloride powder: powdery form
  potassium chloride powder: powdery form Addition-reaction inhibitor: 1-ethynylcyclohexanol Preparation Example 1

The graphite was dispersed in methanol containing the sodium chloride powder at 1 mass %. The resulting 10-mass % graphite dispersion was stirred at 60° C. for 10 hours. The methanol was then evaporated. Thereby, Ion-treated graphite 1 was prepared.

Preparation Example 2

DENKA BLACK Li-400 was dispersed in methanol containing the sodium chloride powder at 1 mass %. The resulting 10-mass % carbon black dispersion was stirred at 60° C. for 10 hours. The methanol was then evaporated. Thereby, Ion-treated carbon black 1 was prepared.

Preparation Example 3

Ion-treated carbon black 2 was prepared in the same manner as in Preparation Example 2, except that the potassium chloride powder was used instead of the sodium chloride powder.

Examples 1 to 27, Comparative Examples 1 to 3

According to the compositions shown in Tables 1 to 3, the ionic polymers (ion polymers), hydrosilyl group-containing silicones, silicone resin, organic solvents, electric conductivity improvers, and additives (polyglycerins, addition-reaction inhibitor) were blended to prepare the components (A) and (B). The component (C) was added thereto and mixed at ratios shown in Tables 4, 5. The water contents (mass %) of the component (A) (A-Solutions 1 to 26, Comparative A-Solutions 1 to 3) and the component (B) (B-Solutions 1 to 3) were measured according to the Karl Fischer method. Note that the water content of the bio-electrode composition obtained by mixing the components (A), (B), and (C) can be determined from the amounts (parts by mass) of the components (A) and (B) blended and their water contents because the proportion of the component (C) blended is small and water derived therefrom is negligible. In Examples 1 to 27, each of the bio-electrode compositions had a water content of 0.2 mass % or less.

TABLE 1

| A-Solution | Ionic polymer (parts by mass) | Silicone resin (parts by mass) | Electric conductivity improver, Additive (parts by mass) | Organic solvent (parts by mass) | Water content (%) |
|---|---|---|---|---|---|
| A-Solution 1 | Ion polymer 1 (20) | Siloxane compound 1(40) Siloxane compound 2(100) | carbon black(10) 1-ethynylcyclohexanol(3) | ISOPAR G(60) PGMEA(46.6) | 0.03 |
| A-Solution 2 | Ion polymer 2 (20) | Siloxane conpound 1(40) Siloxane compound 2(100) | carbon black(10) 1-ethynylcyclohexanol(3) | ISOPAR G(60) 2-heptanone(46.6) | 0.06 |
| A-Solution 3 | Ion polymer 3 (20) | Siloxane conpound 1(40) Siloxane compound 2(100) | carbon nanotube(3) silver flake(5) 1-ethynylcyclohexanol(3) | ISOPAR G(60) 2-ethoxy carbonyl cyclopentanone(46.6) | 0.05 |
| A-Solution 4 | Ion polymer 4 (20) | Siloxane compound 1(40) Siloxane compound 2(100) | carbon black(10) gold powder(1) 1-ethynylcyclohexanol(3) | ISOPAR G(60) cyclohexanone(46.6) | 0.06 |
| A-Solution 5 | Ion polymer 5 (20) | Siloxane compound 1(40) Siloxane ccupound 2(100) | lithium titanate(12) 1-ethynylcyclohexanol(3) | ISOBAR G(60) cyclopentanone(46.6) | 0.07 |
| A-Solution 6 | Ion polymer 5 (20) | Siloxane compound 1(40) Siloxane compound 2(100) | carbon black(10) 1-ethynylcyclohexanol(3) | ISOPAR G(60) cyclopentanone(46.6) | 0.05 |
| A-Solution 7 | Ion polymer 6 (20) | Siloxane compound 3(126) KF-353(5) | carbon black(10) 1-ethynylcyclohexanol(3) | ISOPAR M(60) 2-propylcyclohexanone (46.6) | 0.05 |
| A-Solution 8 | Ion polymer 7 (20) | Siloxane compound 1(40) Siloxane compound 2(100) | carbon black(10) Polyglycerin silicone 1(2.0) 1-ethynylcyclohexanol(3) | ISOPAR G(60) 2-acetylcyclohexanone (46.6) | 0.15 |
| A-Solution 9 | Ion polymer 8 (20) | Siloxane compound 1(40) Siloxane compound 2(100) | carbon black(10) Polyglycerin silicone 2(2.0) 1-ethynylcyclohexanol(3) | ISOPAR G(60) 2-pentyl -2- cyclopenten-1- one(46.6) | 0.08 |
| A-Solution 10 | Ion polymer 9 (20) | Siloxane compound 3(126) | carbon black(10) Polyglycerin silicone 3(2.0) 1-ethynylcyclohexanol(3) | n-octane(60) 2-heptylcyclopentanone (46.6) | 0.01 |
| A-Solution 11 | Ion polyner 10 (20) | Siloxane compound 3(126) | carbon black(10) Polyglycerin silicone 4(2.0) 1-ethynylcyclohexanol(3) | n-nonane(60) 3,3,5- trimethylcyclohexanone (46.6) | 0.03 |
| A-Solution 12 | Ion polymer 11 (20) | Siloxane compound 3(126) | carbon black(10) Polyglycerin silicone 4(2.0) 1-ethynylcyclohexanol(3) | n-nonane(60) 2-methoxy carbonyl cyclopentanone(46.6) | 0.05 |
| A-Solution 13 | Ion polymer 12 (20) | Siloxane compound 3(126) | carbon black(10) Polyglycerin silicone5(5.0) 1-ethynylcyclohexanol(3) | ISOPAR G(60) γ-valerolactone (46.6) | 0.06 |
| A-Solution 14 | Ion polyner 13 (20) | Siloxane compound 3(126) | carbon black(10) Polyglycerin silicone 5(5.0) 1-ethynylcyclohexanol(3) | di-n-hexyl ether (60) ε-caprolactone (46.6) | 0.06 |
| A-Solution 15 | Ion polymer 5 (20) | — | — | cyclopentanone(46.6) | 0.07 |
| A-Solution 16 | Ion polymer 14 (20) | — | — | cycloheptanone(46.6) | 0.03 |
| A-Solution 17 | Ion polymer 15 (20) | — | — | 3-methylcyclohexanone (46.6) | 0.05 |
| A-Solution 18 | Ion polymer 16 (20) | Siloxane compound 3(126) | carbon black(10) Polyglycerin silicone 5(5.0) 1-ethynylcyclohexanol(3) | ISOPAR M(60) diethylene glycol diethyl ether (46.6) | 0.06 |
| A-Solution 19 | Ion polymer 17 (20) | Siloxane conpound 3(126) | carbon black(10) Polyglycerin silicone 5(5.0) 1-ethynylcyclohexanol(3) | tridecane(60) diethylene glycol methyl butyl ether (46.6) | 0.05 |

TABLE 2

| A-Solution | Ionic polymer (parts by mass) | Silicone resin (parts by mass) | Electric conductivity improver, Additive (parts by mass) | Organic solvent (parts by mass) | Water content (%) |
|---|---|---|---|---|---|
| A-Solution 20 | Ion polymer 18 (20) | Siloxane compound 3 (126) | carbon black(10) Polyglycerin silicone 5(5.0) 1-ethynylcyclohexanol(3) | dodecane (60) diethylene glycol dibutyl ether (46.6) | 0.04 |
| A-Solution 21 | Ion polymer 19 (20) | Siloxane compound 3 (126) | graphite (10) 1-ethynylcyclohexanol(3) | tridecane(60) diethylene glycol butyl ether acetate (46.6) | 0.05 |
| A-Solution 22 | Ion polymer 20 (20) | Siloxane compound 3 (126) | Ion-treated carbon black-1(10) 1-ethynylcyclohexanol(3) | tridecane(60) diethylene glycol butyl ether acetate (46.6) | 0.04 |
| A-Solution 23 | Ion polymer 21 (20) | Siloxane compound 3 (126) | Ion-treated carbon black-2(10) 1-ethynylcyclohexanol(3) | tridecane(60) diethylene glycol butyl ether acetate (46.6) | 0.05 |
| A-Solution 24 | Ion polymer 22 (20) | Siloxane compound 3 (126) | Ion-treated graphite 1(10) 1-ethynylcyclohexanol(3) | tridecane(60) diethylene glycol butyl ether acetate (46.6) | 0.06 |
| A-Solution 25 | Ion polymer 22 (20) | Siloxane compound 3 (126) | carbon black(10) 1-ethynylcyclohexanol(3) sodium chloride powder (1) | tridecane(60) diethylene glycol butyl ether acetate (46.6) | 0.06 |
| A-Solution 26 | Ion polymer 22 (20) | Siloxane compound 3 (126) | carbon black(10) 1-ethynylcyclohexanol(3) sodium chloride powder (1) | tridecane(60) diethylene glycol butyl ether acetate (46.6) | 0.06 |
| Comparative A-Solution 1 | Comparative ion polymer 1 (20) | — | — | cyclopentanone (46.6) | 0.32 |
| Comparative A-Solution 2 | Comparative ion polymer 2 (20) | — | — | PGEE(46.6) | 0.28 |
| Comparative A-Solution 3 | Comparative ion polymer 3 (20) | — | — | diacetone alcohol (46.6) | 0.07 |

TABLE 3

| B-Solution | Hydrosilyl group-containing silicone (parts by mass) | Silicone resin (parts by mass) | Electric conductivity improver, Additive (parts by mass) | Organic solvent (parts by mass) | Water content (%) |
|---|---|---|---|---|---|
| B-Solution 1 | Siloxane compound 4(100) | — | — | — | 0.01 or less |
| B-Solution 2 | Siloxane compound 4(3) | Siloxane compound 1(40) Siloxane compound 2(100) | carbon black(10) 1-ethynylcyclohexanol(3) | ISOPAR 0(60) | 0.01 or less |
| B-Solution 3 | Siloxane compound 4(3) | Siloxane compound 3(126) | carbon black(10) 1-ethynylcyclohexanol(3) | ISOPAR G(60) | 0.01 or less |

(Biological Signal Evaluation)

A thermoplastic urethane (TPU) film ST-604 (manufactured by Bemis Associates Inc.) was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern including a circular portion with a diameter of 2 cm. Then, one of the mixtures (bio-electrode compositions) of the components A to C shown in Tables 1 to 3 was applied onto the circular portion by screen printing one hour after the mixing. The resultant was air-dried at room temperature for 10 minutes, and then baked using an oven at 125° C. for 10 minutes to evaporate the solvent and cured. In this manner, bio-electrodes were prepared (FIG. 3). The urethane film having the bio-electrode printed thereon was cut out and pasted on a double-sided tape. In this manner, three bio-electrodes (bio-electrode samples) were prepared for each of the composition solutions (FIG. 4). Here, FIG. 3 shows the bio-electrodes 1 each including the electro-conductive pattern 2 printed on the thermoplastic urethane film 20 and the cured living body contact layer 3 further prepared thereon. FIG. 4 shows the bio-electrode sample 10 with the double-sided tape 21 pasted on the cut thermoplastic urethane film 20 having the electro-conductive pattern 2 printed thereon and cured.

(Thickness Measurement of Living Body Contact Layer)

The thickness of the living body contact layer of each bio-electrode prepared as described above was measured with a micrometer. Tables 4 and 5 show the result.

(Biological Signal Measurement)

The electro-conductive wiring pattern formed from the electro-conductive paste of each bio-electrode sample was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. The electrocardiogram measurement was started 20 minutes after the attachments to check whether or not an electrocardiogram waveform (ECG signal) including P, Q, R, S, and T waves appeared as shown in FIG. 6 and to observe whether or not a residue of the bio-electrode film was left on the skin after the bio-electrode was peeled. Tables 4, 5 show the result.

TABLE 4

| Example | Component A (parts by mass) | Component B (parts by mass) | Component C (parts by mass) | Film thickness (μm) | ECG signal waveform | Residue on skin after bio-electrode peeling |
|---|---|---|---|---|---|---|
| Example 1 | A-Solution 1 (100) | B-Solution 1 (3) | CAT-PL-56(2.0) | 35 | favorable | none |
| Example 2 | A-Solution 2 (100) | B-Solution 1 (3) | CAT-PL-56(2.0) | 33 | favorable | none |
| Example 3 | A-Solution 3 (100) | B-Solution 1 (3) | CAT-PL-56(2.0) | 38 | favorable | none |
| Example 4 | A-Solution 4 (100) | B-Solution 1 (3) | CAT-PL-56(2.0) | 33 | favorable | none |
| Example 5 | A-Solution 5 (100) | B-Solution 1 (3) | CAT-PL-56(2.0) | 36 | favorable | none |
| Example 6 | A-Solution 6 (100) | B-Solution 1 (3) | CAT-PL-56(2.0) | 30 | favorable | none |
| Example 7 | A-Solution 7 (100) | B-Solution 1 (3) | CAT-PL-56(2.0) | 28 | favorable | none |
| Example 8 | A-Solution 8 (100) | B-Solution 1 (3) | CAT-PL-56(2.0) | 29 | favorable | none |
| Example 9 | A-Solution 9 (100) | B-Solution 1 (3) | CAT-PL-56(2.0) | 31 | favorable | none |
| Example 10 | A-Solution 10 (100) | B-Solution 1 (3) | CAT-PL-56(2.0) | 29 | favorable | none |
| Example 11 | A-Solution 11 (100) | B-Solution 1 (3) | CAT-PL-56(2.0) | 27 | favorable | none |
| Example 12 | A-Solution 12 (100) | B-Solution 1 (3) | CAT-PL-56(2.0) | 27 | favorable | none |
| Example 13 | A-Solution 13 (100) | B-Solution 1 (3) | CAT-PL-56(2.0) | 26 | favorable | none |
| Example 14 | A-Solution 14 (100) | B-Solution 1 (3) | CAT-PL-56(2.0) | 31 | favorable | none |
| Example 15 | A-Solution 15 (67) | B-Solution 2 (100) | CAT-PL-56(2.0) | 30 | favorable | none |
| Example 16 | A-Solution 16 (35) | B-Solution 2 (100) | CAT-PL-56(2.0) | 27 | favorable | none |
| Example 17 | A-Solution 17 (35) | B-Solution 2 (100) | CAT-PL-56(2.0) | 28 | favorable | none |
| Example 18 | A-Solution 15 (35) | B-Solution 3 (100) | CAT-PL-56(2.0) | 31 | favorable | none |

TABLE 5

| Example | Component A (parts by mass) | Component B (parts by mass) | Component C (parts by mass) | Film thickness (μm) | ECG signal waveform | Residue on skin after bio-electrode peeling |
|---|---|---|---|---|---|---|
| Example 19 | A-Solution 18 (100) | B-Solution 1 (3) | CAT-PL-56(2.0) | 35 | favorable | none |
| Example 20 | A-Solution 19 (100) | B-Solution 1 (3) | CAT-PL-56(2.0) | 33 | favorable | none |
| Example 21 | A7Solution 20 (100) | B-Solution 1 (3) | CAT-PL-56(2.0) | 31 | favorable | none |
| Example 22 | A-Solution 21 (100) | B-Solution 1 (3) | CAT-PL-56(2.0) | 30 | favorable | none |
| Example 23 | A-Solution 22 (100) | B-Solution 1 (3) | CAT-PL-56(2.0) | 37 | favorable | none |
| Example 24 | A-Solution 23 (100) | B-Solution 1 (3) | CAT-PL-56(2.0) | 36 | favorable | none |
| Example 25 | A-Solution 24 (100) | B-Solution 1 (3) | CAT-PL-56(2.0) | 34 | favorable | none |
| Example 26 | A-Solution 25 (100) | B-Solution 1 (3) | CAT-PL-56(2.0) | 38 | favorable | none |
| Example 27 | A-Solution 26 (100) | B-Solution 1 (3) | CAT-PL-56(2.0) | 40 | favorable | none |

TABLE 5-continued

| Example | Component A (parts by mass) | Component B (parts by mass) | Component C (parts by mass) | Film thickness (μm) | ECG signal waveform | Residue on skin after bio-electrode peeling |
|---|---|---|---|---|---|---|
| Comparative Example 1 | Comparative A-Solution 1 (35) | B-Solution 2 (100) | CAT-PL-56(2.0) | 32 | favorable | present |
| Comparative Example 2 | Comparative A-Solution 2 (35) | B-Solution 2 (100) | CAT-PL-56(2.0) | 36 | favorable | present |
| Comparative Example 3 | Comparative A-Solution 3 (35) | B-Solution 2 (100) | CAT-PL-56(2.0) | 36 | favorable | present |

As shown in Tables 4 and 5, favorable biological signals were obtained and no residue was left on the skin after the peeling in Examples 1 to 27, in each of which the living body contact layer was formed from the inventive bio-electrode composition prepared by using the solution having a low water content of 0.2% or less, or the solvent containing an ether solvent, an ester solvent, or a ketone solvent but not containing a hydroxy group, a carboxyl group, a nitrogen atom, or a thiol group in the component (A).

In contrast, in the cases where the bio-electrode compositions having a water content exceeding 0.2% were used, and where the solvent containing a hydroxy group was used (DAA), biological signals were obtained, but residues were left on the skin after the peeling (Comparative Examples 1 to 3).

From the foregoing, the bio-electrode including the living body contact layer formed from the inventive bio-electrode composition is excellent in electric conductivity, biocompatibility, and adhesion to the electro-conductive base material, and the ionic conductivity is so high that biological signals can be obtained favorably. Moreover, the inventive bio-electrode leaves no residue on skin after the peeling because the crosslinking reaction sufficiently proceeds in the film without inhibiting the addition reaction.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A bio-electrode composition comprising:
a component (A) comprising an ionic polymer material;
a component (B) comprising an addition reaction-curable silicone having at least a hydrosilyl group;
a component (C) comprising a platinum-group catalyst;
a solvent; and
a water content of 0.2 mass % or less, wherein
the solvent comprises one or more of an ether solvent, an ester solvent, and a ketone solvent each of which does not contain a hydroxy group, a carboxyl group, a nitrogen atom, or a thiol group.

2. The bio-electrode composition according to claim 1, wherein
the component (A) further comprises a solvent;
the component (C) further comprises a solvent, and
the component (A) and the component (B) each have a water content of 0.2 mass % or less.

3. The bio-electrode composition according to claim 2, wherein
the solvent of the component (A) is one or more of (i) an ether solvent, (ii) an ester solvent, and (iii) a ketone solvent, each of which does not contain a hydroxy group, a carboxyl group, a nitrogen atom, or a thiol group, and
the component (B) (i) excludes a solvent or (ii) comprises (a) a hydrocarbon solvent or (b) an ether solvent.

4. The bio-electrode composition according to claim 1, wherein the ionic polymer material of the component (A) is a polymer compound comprising a repeating unit having a structure selected from the group consisting of salts of a sodium, a potassium, and a silver of one or more of fluorosulfonic acid, fluorosulfonimide, and N-carbonyl-fluorosulfonamide.

5. The bio-electrode composition according to claim 4, wherein the structure is shown by any of the following general formulae (1)-1 to (1)-4,

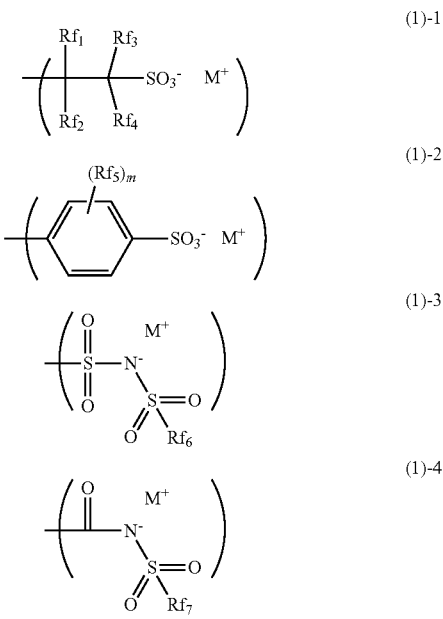

wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, a linear alkyl group having 1 to 4 carbon atoms, or a branched alkyl group having 3 or 4 carbon atoms, and have at least one fluorine atom; "m" represents an integer of 1 to 4; and M represents sodium, potassium, or silver.

6. The bio-electrode composition according to claim 5, wherein one or more repeating units having structures selected from the group consisting of salts of a sodium, a potassium, and a silver of fluorosulfonic acid shown by the general formula (1)-1 or (1)-2, sulfonimide shown by (1)-3, or sulfonamide shown by (1)-4 comprise at least one repeating unit selected from the group consisting of repeating units-a1 to -a7 shown by the following general formula (2),

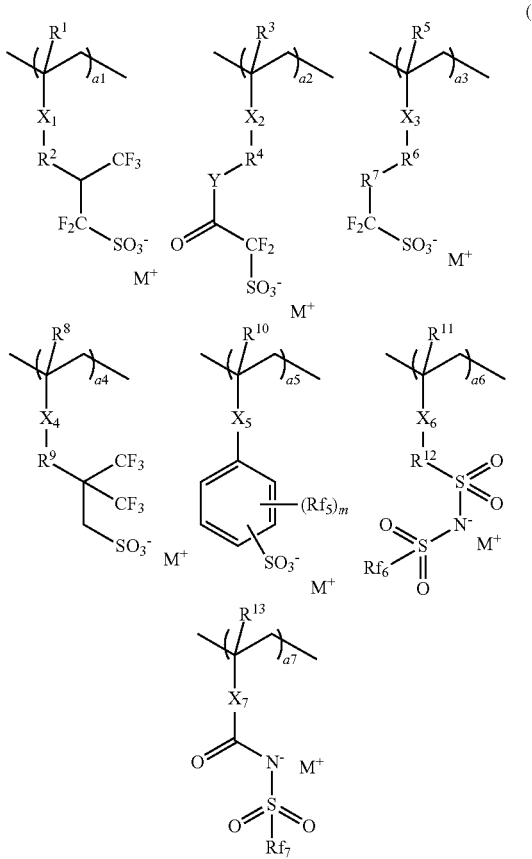

(2)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, a linear divalent hydrocarbon group having 1 to 13 carbon atoms, and a branched or cyclic divalent hydrocarbon group having 3 to 12 carbon atoms, the divalent hydrocarbon groups optionally having either or both of an ether group and an ester group; $R^7$ represents a linear alkylene group having 1 to 4 carbon atoms or a branched alkylene group having 3 to 12 carbon atoms, and one or two hydrogen atoms in $R^7$ are optionally substituted with a fluorine atom; $X_1$, $X_2$, $X_3$, $X_4$, and $X_6$ each independently represent any of a single bond, a phenylene group, a naphthylene group, an ether group, an ester group, and an amide group; $X_5$ represents any of a single bond, an ether group, and an ester group; $X_7$ represents a single bond, an arylene group having 6 to 12 carbon atoms, or —C(=O)—O—$X_{10}$—; $X_{10}$ represents a linear, branched, or cyclic alkylene group having 1 to 12 carbon atoms, or a divalent aromatic hydrocarbon group having 6 to 10 carbon atoms, and $X_{10}$ optionally contains an ether group, a carbonyl group, or an ester group; Y represents an oxygen atom or a —$NR^{19}$— group, optionally bonded to $R^4$ to form a ring; $R^{19}$ represents a hydrogen atom, a linear alkyl group having 1 to 4 carbon atoms, or a branched alkyl group having 3 or 4 carbon atoms; "m" represents an integer of 1 to 4; a1, a2, a3, a4, a5, a6, and a7 represent numbers satisfying $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$; and M, $Rf_5$, $Rf_6$, and $Rf_7$ are as defined above.

7. The bio-electrode composition according to claim 1, wherein the component (B) comprises organopolysiloxane having a hydrosilyl group.

8. The bio-electrode composition according to claim 1, wherein the component (B) comprises organopolysiloxane having a hydrosilyl group and diorganopolysiloxane having an alkenyl group.

9. The bio-electrode composition according to claim 1, wherein
the component (B) further comprises a silicone resin having an $SiO_2$ unit and an $R_xSiO_{(4-x)/2}$ unit, wherein
R represents a substituted or unsubstituted monovalent hydrocarbon group having 1 to 10 carbon atoms, and
"x" represents a number in a range of 2.5 to 3.5.

10. The bio-electrode composition according to claim 1, wherein the component (A) comprises diorganosiloxane having an alkenyl group in addition to the ionic polymer material.

11. The bio-electrode composition according to claim 10, wherein the component (A) further comprises a silicone resin having an $SiO_2$ unit and an $R_xSiO_{(4-x)/2}$ unit, wherein
R represents a substituted or unsubstituted monovalent hydrocarbon group having 1 to 10 carbon atoms, and
"x" represents a number in a range of 2.5 to 3.5.

12. The bio-electrode composition according to claim 1, further comprising a component (D) in the component (A) or (B), the component (D) being one or more selected from the group consisting of carbon powder, metal powder, silicon powder, lithium titanate powder, and metal chloride powder.

13. The bio-electrode composition according to claim 12, wherein the carbon powder is any of carbon black, graphite, and carbon nanotube, or a combination thereof.

14. The bio-electrode composition according to claim 13, wherein the carbon powder further comprises an ion component.

15. The bio-electrode composition according to claim 12, wherein the metal powder is a powder of a metal selected from the group consisting of gold, silver, platinum, copper, tin, titanium, nickel, aluminum, tungsten, molybdenum, ruthenium, chromium, and indium.

16. The bio-electrode composition according to claim 15, wherein the metal powder is a silver powder.

17. A method for producing the bio-electrode composition according to claim 1, comprising:
storing (A) the ionic polymer material, (B) the addition reaction-curable silicone having at least a hydrosilyl group, and (C) the platinum-group catalyst in separate containers; and
mixing these components to produce a bio-electrode composition when a bio-electrode is manufactured.

18. A method for producing the bio-electrode composition according to claim 12, wherein the component (D) mixes into the component (A) or (B) before or at the same time when blending the component (C).

19. A bio-electrode comprising an electro-conductive base material and a living body contact layer formed on the electro-conductive base material, wherein
the living body contact layer is a cured product of the bio-electrode composition according to claim 1.

20. The bio-electrode according to claim 19, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

21. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition to form the living body contact layer.

22. The method for manufacturing a bio-electrode according to claim 21, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

* * * * *